(12) United States Patent
Laing et al.

(10) Patent No.: US 9,134,307 B2
(45) Date of Patent: *Sep. 15, 2015

(54) METHOD FOR DETERMINING ION CHANNEL MODULATING PROPERTIES OF A TEST REAGENT

(75) Inventors: Lance G. Laing, Belmont, MA (US); Rick Wagner, Cambridge, MA (US); Rafael Fernandez, Jamaica Plain, MA (US); Alexander Yuzhakov, West Roxbury, MA (US)

(73) Assignee: X-Body, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/335,433

(22) Filed: Dec. 15, 2008

(65) Prior Publication Data

US 2009/0137422 A1 May 28, 2009

Related U.S. Application Data

(63) Continuation-in-part of application No. 12/171,475, filed on Jul. 11, 2008.

(60) Provisional application No. 60/949,142, filed on Jul. 11, 2007, provisional application No. 61/043,478, filed on Apr. 9, 2008.

(51) Int. Cl.
*C12Q 1/04* (2006.01)
*G01N 33/543* (2006.01)
*G01N 33/68* (2006.01)

(52) U.S. Cl.
CPC ............ *G01N 33/54373* (2013.01); *C12Q 1/04* (2013.01); *G01N 33/6872* (2013.01)

(58) Field of Classification Search
CPC ........................................................ C12Q 1/04
USPC ........................................................... 435/29
See application file for complete search history.

(56) References Cited

U.S. PATENT DOCUMENTS

| | | | |
|---|---|---|---|
| 3,689,346 A | 9/1972 | Rowland | |
| 3,810,688 A | 5/1974 | Ballman et al. | |
| 3,856,404 A | 12/1974 | Hershler et al. | |
| 4,009,933 A | 3/1977 | Firester | |
| 4,050,895 A | 9/1977 | Hardy et al. | |
| 4,240,751 A | 12/1980 | Linnecke et al. | |
| 4,289,371 A | 9/1981 | Kramer | |
| 4,344,438 A | 8/1982 | Schultz | |
| 4,420,502 A | 12/1983 | Conley | |
| 4,536,608 A | 8/1985 | Sheng et al. | |
| 4,560,248 A | 12/1985 | Cramp | |
| 4,576,850 A | 3/1986 | Martens | |
| 4,608,344 A | 8/1986 | Carter et al. | |
| 4,650,329 A | 3/1987 | Barrett et al. | |
| 4,652,290 A | 3/1987 | Cho et al. | |
| 4,668,558 A | 5/1987 | Barber | |
| 4,701,008 A | 10/1987 | Richard et al. | |
| 4,810,658 A | 3/1989 | Shanks et al. | |
| 4,815,843 A | 3/1989 | Tiefenthaler et al. | |
| 4,818,710 A | 4/1989 | Sutherland et al. | |
| 4,857,273 A | 8/1989 | Stewart et al. | |
| RE33,064 E | 9/1989 | Carter | |
| 4,876,208 A | 10/1989 | Gustafson et al. | |
| 4,882,288 A | 11/1989 | North et al. | |
| 4,888,260 A | 12/1989 | Cowan | |
| 4,931,384 A | 6/1990 | Layton et al. | |
| 4,952,056 A | 8/1990 | Tiefenthaler | |
| 4,958,895 A | 9/1990 | Wells et al. | |
| 4,992,385 A | 2/1991 | Godfrey | |
| 4,999,234 A | 3/1991 | Cowan | |
| 5,071,248 A | 12/1991 | Tiefenthaler et al. | |
| 5,118,608 A | 6/1992 | Layton et al. | |
| 5,155,785 A | 10/1992 | Holland et al. | |
| 5,156,785 A | 10/1992 | Zdrahala | |
| 5,170,448 A | 12/1992 | Ackley et al. | |
| 5,175,030 A | 12/1992 | Lu | |
| 5,210,404 A | 5/1993 | Cush et al. | |
| 5,216,680 A | 6/1993 | Magnusson | |
| 5,229,614 A | 7/1993 | Andersson et al. | |
| 5,242,828 A | 9/1993 | Bergström et al. | |
| 5,268,782 A | 12/1993 | Wenz et al. | |
| 5,310,686 A | 5/1994 | Sawyers et al. | |
| 5,337,183 A | 8/1994 | Rosenblatt | |
| 5,413,884 A | 5/1995 | Koch et al. | |
| 5,442,169 A | 8/1995 | Kunz | |
| 5,455,178 A | 10/1995 | Fattinger | |
| 5,475,780 A | 12/1995 | Mizrahi | |
| 5,478,527 A | 12/1995 | Gustafson et al. | |

(Continued)

FOREIGN PATENT DOCUMENTS

| | | |
|---|---|---|
| CA | 2394966 | 8/2001 |
| CA | 2395318 | 8/2001 |

(Continued)

OTHER PUBLICATIONS

Bandell (Mar. 24, 2004) Neuron vol. 41 pp. 849 to 857 Supplemental Figure S1.*
Bandell (Mar. 24, 2004) Neuron vol. 41 pp. 849 to 857 Supplemental Figure S2.*
Bandell (Mar. 24, 2004) Neuron vol. 41 pp. 849 to 857 Supplemental Table 1.*
Bandell (Mar. 24, 2004) Neuron vol. 41 pp. 849 to 857 (including Supplemental Figures S1-S2 and Table 1).*
Cunningham (Sep. 2004) Journal of Biomolecular Screening vol. 9 pp. 481.*
Petrunkina et al., Journal of Cellular Physiology, vol. 204, pp. 508-521 (2005).*
Reckless and Grainger, "Identification of oligopeptide sequences which inhibit migration induced by a wide range of chemokines", Biochem. J., 340:803-811 (1999).

(Continued)

*Primary Examiner* — Ardin Marschel
(74) *Attorney, Agent, or Firm* — McDonnell Boehnen Hulbert & Berghoff LLP

(57) ABSTRACT

The invention provides methods for identifying modulators of ion channels without the use of recombinant cell lines over-expressing the ion channel proteins or the use of detection labels.

17 Claims, 3 Drawing Sheets

(56) References Cited

U.S. PATENT DOCUMENTS

| | | |
|---|---|---|
| 5,478,756 A | 12/1995 | Gizeli et al. |
| 5,492,840 A | 2/1996 | Malmquist et al. |
| 5,496,701 A | 3/1996 | Pollard-Knight |
| 5,559,338 A | 9/1996 | Elliott et al. |
| 5,598,267 A | 1/1997 | Sambles et al. |
| 5,598,300 A | 1/1997 | Magnusson et al. |
| 5,601,997 A | 2/1997 | Tchao |
| 5,606,170 A | 2/1997 | Saaski et al. |
| 5,615,052 A | 3/1997 | Doggett |
| 5,629,214 A | 5/1997 | Crosby |
| 5,631,171 A | 5/1997 | Sandstrom et al. |
| 5,666,197 A | 9/1997 | Guerra |
| 5,690,894 A | 11/1997 | Pinkel et al. |
| 5,691,846 A | 11/1997 | Benson et al. |
| 5,732,173 A | 3/1998 | Bylander et al. |
| 5,738,825 A | 4/1998 | Rudigier et al. |
| 5,768,461 A | 6/1998 | Svetkoff et al. |
| 5,771,328 A | 6/1998 | Wortman et al. |
| 5,792,411 A | 8/1998 | Morris et al. |
| 5,801,390 A | 9/1998 | Shiraishi |
| 5,804,453 A | 9/1998 | Chen |
| 5,814,516 A | 9/1998 | Vo-Dinh |
| 5,814,524 A | 9/1998 | Walt et al. |
| 5,821,343 A | 10/1998 | Keogh |
| 5,846,843 A | 12/1998 | Simon |
| 5,864,641 A | 1/1999 | Murphy et al. |
| 5,922,550 A | 7/1999 | Everhart et al. |
| 5,925,878 A | 7/1999 | Challener |
| 5,955,335 A | 9/1999 | Thust et al. |
| 5,955,378 A | 9/1999 | Challener |
| 5,955,729 A | 9/1999 | Nelson |
| 5,986,762 A | 11/1999 | Challener |
| 5,991,480 A | 11/1999 | Kunz et al. |
| 5,994,150 A | 11/1999 | Challener et al. |
| 5,998,298 A | 12/1999 | Hetherington et al. |
| 6,035,089 A | 3/2000 | Grann et al. |
| 6,042,998 A | 3/2000 | Brueck et al. |
| 6,052,213 A | 4/2000 | Burt et al. |
| 6,076,248 A | 6/2000 | Hoopman et al. |
| 6,088,505 A | 7/2000 | Hobbs |
| 6,100,991 A | 8/2000 | Challener |
| 6,128,431 A | 10/2000 | Siminovitch |
| 6,146,593 A | 11/2000 | Pinkel et al. |
| 6,174,677 B1 | 1/2001 | Vo-Dinh |
| 6,185,019 B1 | 2/2001 | Hobbs et al. |
| 6,200,737 B1 | 3/2001 | Walt et al. |
| 6,215,928 B1 | 4/2001 | Friesem et al. |
| 6,218,194 B1 | 4/2001 | Lyndin et al. |
| 6,235,488 B1 | 5/2001 | Tom-Moy et al. |
| 6,303,179 B1 | 10/2001 | Koulik et al. |
| 6,316,153 B1 | 11/2001 | Goodman et al. |
| 6,320,991 B1 | 11/2001 | Challener et al. |
| RE37,473 E | 12/2001 | Challener |
| 6,332,663 B1 | 12/2001 | Puzio et al. |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. |
| 6,395,558 B1 | 5/2002 | Duveneck et al. |
| 6,404,554 B1 | 6/2002 | Lee et al. |
| 6,449,097 B1 | 9/2002 | Zhu et al. |
| 6,558,957 B1 | 5/2003 | Roinestad et al. |
| 6,570,657 B1 | 5/2003 | Hoppe et al. |
| 6,579,673 B2 | 6/2003 | McGrath et al. |
| 6,587,276 B2 | 7/2003 | Daniell |
| 6,661,952 B2 | 12/2003 | Simpson et al. |
| 6,707,561 B1 | 3/2004 | Budach et al. |
| 6,748,138 B2 | 6/2004 | Wang et al. |
| 6,771,376 B2 | 8/2004 | Budach et al. |
| 6,867,869 B2 | 3/2005 | Budach et al. |
| 6,870,624 B2 | 3/2005 | Hobbs et al. |
| 6,870,630 B2 | 3/2005 | Budach et al. |
| 6,902,703 B2 | 6/2005 | Marquiss et al. |
| 6,951,715 B2 | 10/2005 | Cunningham |
| 6,982,171 B2 | 1/2006 | Kim |
| 6,989,542 B2 * | 1/2006 | Moses et al. ............. 250/440.11 |
| 6,990,259 B2 | 1/2006 | Cunningham |
| 7,018,838 B2 | 3/2006 | Murphy |
| 7,023,544 B2 | 4/2006 | Cunningham |
| 7,033,819 B2 | 4/2006 | Kim |
| 7,033,821 B2 | 4/2006 | Kim |
| 7,064,844 B2 | 6/2006 | Budach et al. |
| 7,070,987 B2 | 7/2006 | Cunningham |
| 7,074,311 B1 | 7/2006 | Cunningham |
| 7,094,595 B2 | 8/2006 | Cunningham |
| 7,101,660 B2 | 9/2006 | Cunningham et al. |
| 7,118,710 B2 | 10/2006 | Cunningham |
| 7,142,296 B2 | 11/2006 | Cunningham et al. |
| 7,148,964 B2 | 12/2006 | Cunningham et al. |
| 7,153,702 B2 | 12/2006 | Lin |
| 7,158,230 B2 | 1/2007 | Cunningham |
| 7,162,125 B1 | 1/2007 | Schulz |
| 7,170,599 B2 | 1/2007 | Cunningham et al. |
| 7,175,980 B2 | 2/2007 | Qiu et al. |
| 7,197,198 B2 | 3/2007 | Schulz |
| 7,202,076 B2 | 4/2007 | Cunningham et al. |
| 7,217,574 B2 | 5/2007 | Pien et al. |
| 7,264,973 B2 | 9/2007 | Lin et al. |
| 7,267,993 B2 | 9/2007 | Pentrenko |
| 7,292,336 B2 | 11/2007 | Cunningham et al. |
| 7,298,477 B1 | 11/2007 | Cunningham et al. |
| 7,300,803 B2 | 11/2007 | Lin et al. |
| 7,301,628 B2 | 11/2007 | Cunningham et al. |
| 7,306,827 B2 | 12/2007 | Li et al. |
| 7,309,614 B1 | 12/2007 | Baird |
| 7,312,090 B2 | 12/2007 | Lin et al. |
| 7,327,454 B2 | 2/2008 | Cunningham et al. |
| 7,396,675 B2 | 7/2008 | Pawlak et al. |
| 7,400,399 B2 | 7/2008 | Wawro et al. |
| 7,479,404 B2 | 1/2009 | Cunningham |
| 7,483,127 B1 | 1/2009 | Li |
| 7,497,992 B2 | 3/2009 | Cunningham |
| 7,521,769 B2 | 4/2009 | Cunningham |
| 7,524,625 B2 | 4/2009 | Madison |
| 7,534,578 B1 | 5/2009 | Baird |
| 7,620,276 B2 | 11/2009 | Schulz |
| 7,628,085 B2 | 12/2009 | Laing |
| 7,678,548 B2 * | 3/2010 | Brown et al. ................ 435/7.21 |
| 7,742,662 B2 | 6/2010 | Cunningham |
| 7,756,365 B2 | 7/2010 | Cunningham |
| 7,790,406 B2 | 9/2010 | Cunningham |
| 2002/0018610 A1 | 2/2002 | Challener et al. |
| 2002/0028045 A1 | 3/2002 | Yoshimura |
| 2002/0028480 A1 | 3/2002 | Maher et al. |
| 2002/0076747 A1 | 6/2002 | Price |
| 2002/0123050 A1 | 9/2002 | Poponin |
| 2002/0127565 A1 | 9/2002 | Cunningham et al. |
| 2002/0135752 A1 | 9/2002 | Sokolov et al. |
| 2002/0168295 A1 | 11/2002 | Cunningham et al. |
| 2002/0171045 A1 | 11/2002 | Perraut |
| 2003/0003599 A1 | 1/2003 | Wagner et al. |
| 2003/0017580 A1 | 1/2003 | Cunningham et al. |
| 2003/0017581 A1 | 1/2003 | Li et al. |
| 2003/0026891 A1 | 2/2003 | Qiu et al. |
| 2003/0027327 A1 | 2/2003 | Cunningham et al. |
| 2003/0027328 A1 | 2/2003 | Cunningham et al. |
| 2003/0032039 A1 | 2/2003 | Cunningham et al. |
| 2003/0059855 A1 | 3/2003 | Cunningham et al. |
| 2003/0068657 A1 | 4/2003 | Lin et al. |
| 2003/0077660 A1 | 4/2003 | Pien et al. |
| 2003/0092075 A1 | 5/2003 | Pepper |
| 2003/0104479 A1 | 6/2003 | Bright |
| 2003/0108954 A1 | 6/2003 | Mutz |
| 2003/0113766 A1 | 6/2003 | Pepper et al. |
| 2003/0148542 A1 | 8/2003 | Pawlak |
| 2003/0210396 A1 | 11/2003 | Hobbs et al. |
| 2003/0224369 A1 | 12/2003 | Surber et al. |
| 2004/0005540 A1 | 1/2004 | Pentrenko |
| 2004/0011965 A1 | 1/2004 | Hodgkinson |
| 2004/0091397 A1 | 5/2004 | Picard |
| 2004/0132172 A1 | 7/2004 | Cunningham et al. |
| 2004/0132214 A1 | 7/2004 | Lin et al. |
| 2004/0151626 A1 | 8/2004 | Cunningham et al. |
| 2004/0191757 A1 | 9/2004 | Maher |

(56) References Cited

U.S. PATENT DOCUMENTS

| | | | |
|---|---|---|---|
| 2004/0204357 A1* | 10/2004 | Brautigam et al. | 514/12 |
| 2004/0219619 A1 | 11/2004 | Fernandez-Salas | |
| 2005/0058639 A1 | 3/2005 | Gudas | |
| 2005/0074825 A1 | 4/2005 | Luo | |
| 2005/0214803 A1 | 9/2005 | Wang | |
| 2005/0221271 A1 | 10/2005 | Murphy | |
| 2005/0227374 A1 | 10/2005 | Cunningham | |
| 2006/0003372 A1 | 1/2006 | Li | |
| 2006/0030033 A1 | 2/2006 | Cunningham | |
| 2006/0040376 A1 | 2/2006 | Cunningham et al. | |
| 2006/0057707 A1 | 3/2006 | Lin et al. | |
| 2006/0181705 A1 | 8/2006 | Cunningham | |
| 2006/0193550 A1 | 8/2006 | Wawro et al. | |
| 2006/0275825 A1 | 12/2006 | Laing | |
| 2006/0281077 A1 | 12/2006 | Lin | |
| 2006/0286663 A1 | 12/2006 | Cunningham et al. | |
| 2007/0015210 A1 | 1/2007 | Ezekiel | |
| 2007/0041012 A1 | 2/2007 | Cunningham et al. | |
| 2007/0054339 A1 | 3/2007 | Lin | |
| 2007/0070355 A1 | 3/2007 | Cunningham et al. | |
| 2007/0141231 A1 | 6/2007 | Cunningham et al. | |
| 2007/0299029 A1 | 12/2007 | Zhuo | |
| 2008/0213910 A1 | 9/2008 | Jogikalmath | |
| 2008/0219892 A1 | 9/2008 | Cunningham | |
| 2008/0240543 A1 | 10/2008 | Budach | |
| 2008/0299673 A1 | 12/2008 | Laing | |
| 2009/0017488 A1 | 1/2009 | Binder et al. | |
| 2009/0130703 A1 | 5/2009 | Wagner et al. | |
| 2009/0137422 A1 | 5/2009 | Laing | |
| 2009/0148955 A1 | 6/2009 | Cunningham | |
| 2009/0176658 A1 | 7/2009 | Madison | |
| 2009/0179637 A1 | 7/2009 | Cunningham | |
| 2009/0192049 A1 | 7/2009 | Laing | |
| 2009/0227469 A1 | 9/2009 | Conklin | |
| 2009/0264314 A1 | 10/2009 | Cunningham | |
| 2009/0269244 A1 | 10/2009 | Cunningham | |
| 2009/0282931 A1 | 11/2009 | Laing | |
| 2009/0305304 A1 | 12/2009 | Laing | |
| 2010/0003743 A1 | 1/2010 | Schulz | |
| 2010/0008826 A1 | 1/2010 | Schulz | |
| 2010/0015721 A1 | 1/2010 | Laing | |
| 2010/0043571 A1 | 2/2010 | Laing | |
| 2010/0143959 A1 | 6/2010 | Cunningham | |
| 2010/0195099 A1 | 8/2010 | Rockney | |
| 2010/0196925 A1 | 8/2010 | Genick | |
| 2010/0202923 A1 | 8/2010 | Cunningham | |
| 2010/0227769 A1 | 9/2010 | Schulz | |
| 2010/0231907 A1 | 9/2010 | Pien | |
| 2010/0291575 A1 | 11/2010 | Shamah | |

FOREIGN PATENT DOCUMENTS

| | | |
|---|---|---|
| CH | 6 690 50 A5 | 2/1989 |
| CH | 6 705 21 A5 | 6/1989 |
| EP | 0 075 353 | 3/1983 |
| EP | 0 112 721 | 7/1984 |
| EP | 0 326 219 | 1/1989 |
| EP | 0 517 777 | 5/1996 |
| EP | 0 660 924 | 9/1999 |
| EP | 1031828 | 8/2000 |
| EP | 1085315 | 3/2001 |
| FR | 2 801 977 | 12/1999 |
| GB | 2 156 970 A | 10/1985 |
| GB | 2 227 089 | 7/1990 |
| JP | 1993-228946 | 9/1993 |
| WO | WO 81/00912 | 2/1981 |
| WO | WO 84/02578 | 7/1984 |
| WO | WO 86/07149 | 12/1986 |
| WO | WO 90/08313 | 7/1990 |
| WO | WO 91/13339 | 9/1991 |
| WO | WO 92/04653 | 3/1992 |
| WO | WO 92/21768 | 12/1992 |
| WO | WO 93/14392 | 7/1993 |
| WO | WO 95/03538 | 2/1995 |
| WO | WO 96/38726 | 12/1996 |
| WO | WO 97/29362 | 8/1997 |
| WO | WO 98/10288 | 3/1998 |
| WO | WO 98/57200 | 12/1998 |
| WO | WO 99/09392 | 2/1999 |
| WO | WO 99/09396 | 2/1999 |
| WO | WO 99/54714 | 10/1999 |
| WO | WO 99/66330 | 12/1999 |
| WO | WO 00/23793 | 4/2000 |
| WO | WO 00/29830 | 5/2000 |
| WO | WO 01/02839 | 1/2001 |
| WO | WO 01/04697 | 1/2001 |
| WO | WO 01/79559 | 10/2001 |
| WO | WO 01/92870 | 12/2001 |
| WO | WO 02/061429 | 8/2002 |
| WO | 03/074548 | 9/2003 |
| WO | 2007056160 | 5/2007 |
| WO | 2007/064702 | 6/2007 |
| WO | 2009/009718 | 1/2009 |
| WO | 2010005600 | 1/2010 |
| WO | 2010/075033 | 7/2010 |

OTHER PUBLICATIONS

Jackson, et al., "Pharmacologic Actions of the Second-Generation Leukotriene B4 Receptor Antagonist LY293111: In Vitro Studies", The Journal of Pharmacology and Experimental Therapeutics, vol. 288, No. 1, 288:286-294 (1999).

Taguchi et al., "Patterns for RANTES Secretion and Intercellular Adhesion Molecule 1 Expression Mediate Transepithelial T Cell Traffic Based on Analyses In Vitro and In Vivo", J. Exp. Med., vol. 187, No. 12, p. 1927-1940 (1998).

Dharmawardhane et al., "Localization of p21-Activated Kinase 1 (PAK1) to Pinocytic Vesicles and Cortical Actin Structures in Stimulated Cells", The Journal of Cell Biology, vol. 138, No. 6, p. 1265-1278 (1997).

Calderwood, "Integrin activation", Journal of Cell Science, 117:657-666 (2004).

Fleming et al., "PDE4-regulated cAMP degradation controls the assembly of integrin-dependent actin adhesion structures and REF52 cell migration", Journal of Cell Science, 117:2377-2388 (2004).

Mammoto et al., "Role of RhoA, mDia and Rock in cell Shape-dependent Control of the Skp2-p27(kip1) Pathway and the G1/S Transition", The Journal of Biological Chemistry, 279:26323-26330 (2004).

Desire et al., "RAC1 Inhibition Targets Amyloid Precursor Protein Processing by γ-Secretase and Decreases AB Production in Vitro and in Vivo", The Journal of Biological Chemistry, vol. 280, No. 45, p. 37516-37525 (2005).

Kim et al., "Chemokines: signal lamps for trafficking of T and B cells for development and effector function", Journal of Leukocyte Biology, 65:6-15 (1999).

Montresor et al., "Comparative Analysis of Normal versus CLL B-Lymphocytes Reveals Patient-Specific Variability in Signaling Mechanisms Controlling LFA-1 Activation by Chemokines", Cancer Res. 69(24):9281-9290 (2009).

Pelish et al., "Secramine inhibits Cdc42-deopendent functions in cells and Cdc42 activation in vitro", Nature Chemical Biology, 2:39-46 (2006).

Buckley et al., "Cel adhesion: more than just glue (Review)", Molecular Membrane Biology, 15:167-176 (1998).

Takeda et al., "The Integrins", Genome Biology, 8:215 (2007).

Sancho et al., "Binding kinetics of monomeric and aggregated IgG to Kupffer cells and hepatocytes of mice", Immunology, 53:283 (1984).

Chaplen et al., "Improvement of Bioactive Compound Classification through Integration of Orthogonal Cell-Based Biosensing Methods", Sensors, 7:38-51 (2007).

U.S. Appl. No. 13/166,936, filed Jun. 23, 2011.
U.S. Appl. No. 13/073,233, filed Mar. 28, 2011.
U.S. Appl. No. 12/335,393, filed Dec. 15, 2008.

International Search Report for corresponding application No. PCT/US09/30412 dated Jan. 8, 2009.

Ramsden et al., "Optical Method for Measurement of Number and Shape of Attached Cells in Real Time", Cytometry, vol. 19, pp. 97-102 (1995).

(56) References Cited

OTHER PUBLICATIONS

Li et al., "Measurement of Adhesion and Spreading Kinetics of Baby Hamster Kidney and Hybridoma Cells Using an Integrated Optical Method", Biotechnol. Prog., vol. 10, pp. 520-524 (1994).
Palmer, "Diffraction Gratings, The Crucial Dispersive Component", Spectroscopy, 10(2), pp. 14-15 1995.
Wawro et al., "Optical fiber endface biosensor based on resonances in dielectric waveguide gratings", Biomedical Diagnostic Guidance and Surgical-Assist Systems II, Vo-Dihn et al. eds., Proceedings of SPIE, vol. 3911 (2000), p. 86-94.
Office Action dated Apr. 2, 2007 for U.S. Appl. No. 11/506,639 (now U.S. Patent No. 7,298,477).
Cooper, "Current biosensor technologies in drug discovery", Drug Discovery World Summer 2006, pp. 68-82.
Comley, "Label-Free Detection New biosensors facilitate broader range of drug discovery applications", Drug Discovery World Winter May 2004, pp. 63-74.
Cunningham, "Colorimetric Resonant Reflection as a Direct Biochemical Assay Technique", IEEE, Annual International Conference on Micro Electro Mechanical Systems, MEMS, 2002. Las Vegas, NV Jan. 20-24, 2002.
Extended Abstracts (The 68th Autumn Meeting) The Japan Society of Applied Physics, No. 3, p. 1372 (2007).
U.S. Appl. No. 60/244,312, filed Oct. 30, 2000, Cunningham, et al.
U.S. Appl. No. 60/283,314, filed Apr. 12, 2001, Cunningham, et al.
U.S. Appl. No. 60/303,028, filed Jul. 3, 2001, Cunningham, et al.
Brecht, et al., "Optical probes and transducers", Biosensors & Bioelectronics vol. 10, pp. 923-936 (1995).
Challener, et al., "A multilayer grating-based evanescent wave sensing technique", Sensors and Actuators B, 71, pp. 42-46 (2000).
Cowan, "Aztec surface-relief volume diffractive structure", J. Opt. Soc. Am., vol. 7, No. 8, pp. 1529-1544 (1990).
Cowan, "Holographic honeycomb microlens", Optical Engineering, vol. 24, No. 5, pp. 796-802 (1985).
Cowan, "The Recording and Large Scale Replication of Crossed Holographic Grating Arrays using Multiple Beam Interferometry", SPIE vol. 503, Application, Theory, and Fabrication of Periodic Structures, pp. 120-129 (1984).
Cowan, et al., "The Recording and Replication of Holographic Micropatterns for the Ordering of Photographic Emulsion Grains in Film Systems", J. Imaging Sci., vol. 31, No. 3, pp. 100-107 (1987).
Cunningham, "Optically Based Energy Transduction", Techniques in Analytical Chemistry, pp. 260-291 (1998).
Hobbs, et al., "Automated Interference Lithography Systems for Generation of Sub-Micron Feature Size Patterns", SPIE, vol. 3879, pp. 124-135, (1999).
Huber, et al., "Direct optical immunosensing sensitivity and selectivity)", Sensors and Actuators B, 6, pp. 122-126 (1992).
Jenison, et al., "Interference-based detection of nucleic acid targets on optically coated silicon", Nature Biotechnology, vol. 19, pp. 62-64 (2001).
Jin, et al., "A biosensor concept based on imaging ellipsometry for visualization of biomolecular interactions", Analytical Biochemistry, vol. 232, pp. 69-72 (1995).
Jordan, et al., "Surface Plasmon Resonance Imaging Measurements of Electrostatic Biopolymer Adsorption onto Chemically Modified Gold Surfaces", Analytical Chemistry, vol. 69, No. 7, pp. 1449-1456 (1997).
Lin, et al., "A Porous Silicon-Based Optical Interferometric Biosensor", Science, vol. 278, pp. 840-843 (1997).
Magnusson, et al., "New principle for optical filters", Appl. Phys. Lett., vol. 61, No. 9, pp. 1022-1024 (1992).
Magnusson, et al., "Transmission bandpass guided-mode resonance filters", Applied Optics, vol. 34, No. 35, pp. 8106-8109 (1995).
Morhard, et al., "Immobilization of antibodies in micropatterns for cell detection by optical diffraction", Sensors and Actuators B 70, pp. 232-242 (2000).
Pandey, et al., "Proteomics to study genes and genomes", Nature 405(6788):837-46 (2000).

Patel, et al., "Electrically tuned and polarization insensitive Fabry-Perot etalon with a liquid-crystal film", Appl. Phys. Lett., vol. 58, No. 22, pp. 2491-2493 (1991).
Bertoni, et al., "Frequency-Selective Reflection and Transmission by a Periodic Dielectric Layer", IEEE Transactions on Antennas and Propagation, vol. 37, No. 1, pp. 78-83 (1989).
Brundrett, et al., "Normal-incidence guided-mode resonant grating filters: design and experimental demonstration", Optics Letters, vol. 23, No. 9, pp. 700-702 (1998).
Peng, "Polarization-control Components and Narrow-band Filters Based on Subwavelength Grating Structures" 1996 Statement of Applicants dated May 10, 2004.
Leanu, Torben, Material, Silicon Nitride, 1996, 97, 98.
Cerac, Technical publications: Tantalum Oxide, $Ta_2 O_5$ for Optical Coating, 2000, Cerac, Inc.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
Anderson, et al., "Proteomics: applications in basic and applied biology", Current Opinion in Biotechnology, 2000, 11:408-412.
MacBeath, et al., "Printing Proteins as Microarrays for High-Throughput Function Determination"; Science, vol. 289, pp. 1760-1763, 2000.
deWildt, et al., "Antibody arrays for high-throughput screening of antibody-antigen interactions", Nature Biotechnology, vol. 18, pp. 989-994, 2000.
Cunningham, et al., "A plastic colorimetric resonant optical biosensor for multiparallel detection of label-free biochemical interactions", Sensors and Actuators B, 85 (2002) 219-226.
Caruso, et al., "Quartz Crystal Microbalance Study of DNA Immobilization and Hybridization for Nucleic Acid Sensor Development", Analytical Chemistry, vol. 69, No. 11, pp. 2043-2049, 1997.
Hefti, et al, "Sensitive detection method of dielectric dispersions in aqueous-based, surface-bound macromolecular structures using microwave spectroscopy", Applied Physics Letters, vol. 75, No. 12, pp. 1802-1804, 1999.
Wu, et al., "Bioassay of prostate-specific antigen (PSA) using microcantilevers", Nature Biotechnology, vol. 19, pp. 856-860, 2001.
Wasserman, et al., "Structure and Reactivity of Alkylsiloxane Monolayers Formed by Reaction of Alkyltrichlorosilanes on Silicon Substrates"; Langmuir, 5, 1074-1087, 1989.
Kallury, et al., "X-ray Photoelectron Spectroscopy of Silica Surfaces Treated with Polyfunctional Silanes", Anal. Chem., 60, 169-172, 1988.
Cunningham, et al., "Colorimetric resonant reflection as a direct biochemical assay technique", Sensors and Actuators B, 81 (2002) 316-328.
Mullaney, et al., "Epitope Mapping of Neutralizing Botulinum Neurotoxin A Antibodies by Phage Display", Infection and Immunity, vol. 69, No. 10, pp. 6511-6514, 2001.
Nellen, et al., "Integrated Optical Input Grating Couplers as Biochemical Sensors", Sensors and Actuators, 15 (1988) 285-295.
Lukosz and Tiefenthaler, "Embossing technique for fabricating integrated optical components in hard inorganic waveguiding materials," Optics Letters, vol. 8, pp. 537-539 (1983).
Tiefenthaler and Lukosz, "Integrated optical switches and gas sensors," Optics Letters, vol. 10, pp. 137-139 (1984).
Chabay, "Optical Waveguides," Analytical Chemistry, vol. 54, pp. 1071A-1080A (1982).
Sutherland et al., "Optical Detection of Antibody-Antigen Reactions at a Glass-Liquid Interface," Clin. Chem., vol. 30, pp. 1533-1538 (1984).
Holm and Palik, "Internal-reflection spectroscopy," Laser Focus, vol. 15, pp. 60-65 (Aug. 1979).
Harrick and Loeb, "Multiple Internal Reflection Fluorescence Spectrometry," Analytical Chemistry, vol. 45, pp. 687-691 (1973).
Tien, "Light Waves in Thin Films and Integrated Optics," Applied Optics, vol. 10, pp. 2395-2413 (1971).

(56) References Cited

OTHER PUBLICATIONS

Dakss et al., "Grating Coupler for Efficient Excitation of Optical Guided Waves in Thin Films," *Applied Physics Letters*, vol. 16, pp. 523-525 (1970).

Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984).

English translation of CH 670 521 A5, Jun. 15, 1989.

English translation of CH 669 050 A5, Feb. 15, 1989.

Patel, et al., "Multi-vwavelength Tunable Liquid-Crystal Etalon Filter", *IEEE Photonics Technology Letters*, vol. 3, No. 7, pp. 643-644 (1991).

Patterson, S.D., "Proteomics: the industrialization of protein chemistry", *Current Opinions in Biotechnology*. 11(4):413-8 (2000).

Peng, et al., "Experimental demonstration of resonant anomalies in diffraction from two-dimensional gratings", *Optics Letters* vol. 21, No. 8, pp. 549-551 (1996).

Peng, et al., "Resonant scattering from two-dimensional gratings", *J. Opt. Soc. Am. A.*, vol. 13, No. 5, pp. 993-1005 (1996).

Raguin, et al., "Structured Surfaces Mimic Coating Performance", *Laser Focus World*, pp. 113-117 (1997).

Sigal, et al., "A Self-Assembled Monolayer for the Binding and Study of Histidine-Tagged Proteins by Surface Plasmon Resonance", *Analytical Chemistry*, vol. 68, No. 3, pp. 490-497 (1996).

Wang, et al., "Design of waveguide-grating filters with symmetrical line shapes and low sidebands", *Optical Society of America*, vol. 19, No. 12, 919-921 (1994).

Wang, et al., "Guided-mode resonances in planar dielectric-layer diffraction gratings", *J. Opt. Soc. Am.*, vol. 7, No. 8, pp. 1470-1474 (1990).

Wang, et al., "Theory and applications of guided-mode resonance filter", *Applied Optics*, vol. 32, No. 14, pp. 2606-2613 (1993).

International Search Report for foreign counterpart application PCT/US01/50723, Sep. 17, 2002.

International Search Report for foreign counterpart application PCT/US03/01175, Aug. 18, 2003.

Invitation to Pay Additional Fees in foreign counterpart application PCT/US01/50723, Aug. 30, 2002.

Haidner, "Zero-Order Gratings Used as an Artificial Distributed Index Medium", *Optik, Wissenschaftliche Verlag GmbH, Stuttgart, DE*, vol. 89, No. 3, pp. 107-112, 1992.

Peng, et al., "Experimental Demonstration of Resonant Anomalies in Diffraction from two-Dimensional Gratings", *Optics Letters, Optical Society of America*, vol. 21, No. 9, pp. 549-551, 1996.

Wilson, et al., "The Optical Properties 1-19 of 'Moth Eye' Antireflection Surfaces"; *Optica ACTA*, vol. 29, No. 7, pp. 993-1009, 1982.

Bagnich, et al., "*Tunable Optical Filter*", Derwent Publications, English Translation, Abstract Only, Derwent Publications Ltd. (1989).

*Coming, Inc. v. SRU Biosystems, Inc.*, Memorandum Opinion dated Nov. 15, 2005 in the United States District Court for the district of Delaware.

Liu, et al., "*Development of an optical fiber lactate sensor*", Mikrochimica Acta, 1999, 131(1-2), pp. 129-135.

U.S. Appl. No. 11/635,934, filed Dec. 8, 2006.

U.S. Appl. No. 11/566,818, filed Dec. 5, 2006.

U.S. Appl. No. 11/506,639, filed Aug. 18, 2007.

U.S. Appl. No. 11/749,073, filed May 15, 2007.

U.S. Appl. No. 11/828,076, filed Jul. 25, 2007.

European Search Report for EP 07 11 8355 dated Feb. 5, 2008.

Nelson, et al., "BIA/MS of Epitope-Tagged Peptides Directly from *E. coli* Lysate: Multiplex Detection and Protein Identification at Low-Femtomole to Subfemtomole Levels" Anal. Chem. 1999, 71, 2858-2865.

Moffatt, "Optical Probes May Hasten Shift of Diagnostics from Lab to Doc's Office" Genetic Engineering News, vol. 18 (1986) p. 18.

Williams, et al., "The integration of SPR biosensors with mass spectrometry: possible applications for proteome analysis", Trends in Microbiology, Elsevier, vol. 18, No. 2, (2000) pp. 45-48.

Cekaite, et al., "Analysis of the humoral immune response to immunoselected phage-displayed peptides by a microarray-based method", Proteomics 2004, 4, 2572-2582.

Sun, et al., "Use of bioluminescent *Salmonella* for assessing the efficiency of constructed phage-based biosorbent", Journal of Industrial Microbiology & Biotechnology, 2000, 25, 273-275.

Wan, et al., "Landscape phage-based magnetostrictive biosensor for detecting *Bacillus anthracis* spores", Proc. IEEE Sens., 2005, 1308-1311.

Cunningham, et al. "Label-Free Assays on the BIND System", The Society for Biomolecular Screening, p. 481490 (2004).

Cunningham, "Label-Free Detection with the BIND System", Presented at Screentech General, Mar. 24, 2003.

Baird, "Beyond ELISA's: Label-free Detection with BIND", Presented at Interphex Meeting in Europe, Mar. 16-18, 2004.

Cunningham, et al., "Colorimetric Resonant Reflection as a Direct Biochemical Assay Technique", Presented at the Pittsburgh Conference and Exposition on Anayltical Chemistry and Applied Spectroscopy, Morial Convention Center in New Orleans, LA, Mar. 17-22, 2002.

Broad, et al. "Growth and adipose differentiation of sheep preadipocyte fibroblasts in serum-free medium", Eur. J. Bichem, 135, 33-39 (1983).

Castillo et al., "Characterization of proliferation and differentiation of EGF-responsive striatal and septal precursor cells", Int. J. Devl. Neuroscience 21 (2003) 41-47.

Chalazonitis, et al., "The α1 Subunit of Laminin-1 Promotes the Development of Neurons by Interacting with LBP110 Expressed by Neural Crest-Derived Cells Immunoselected from the Fetal Mouse Gut". J. Neurobiol. 33:118-138. 1997.

Hao et al., "Fetal Human Hemotopoietic Stem Cells Can Differentiate Sequentially into Neural Stem Cells and Then Astrocytes in Vitro", Journal of Hematotherapy & Stem Cell Research, 12:23-32 (12003).

Kano, et al., "Establishment of Hepatic Stem-like Cell Lines from Normal Adult Porcine Liver in a Poly-D-Lysine-Coated Dish with Nair-1 Medium", In Vitro Cell. Dev. Biol.—Animal, 30:440-448 (2003).

Sung, et al., "Adhesiveness of Human Ligament Fibroblasts to Laminin", Journal of Orthopaedic Research, 13:166-173 1995.

Zhou, et al., "Long-term nonpassaged EGF-responsive neural precursor cells are stem cells", Wound Repair and Regeneration, vol. 6, No. 4, pp. 337-348 1998.

Adamczyk, et al., "Application of Surface Plasmon Resonance toward Studies of Low-Molecular-Weight Antigen-Antibody Binding Interactions", Methods, 20, pp. 319-328 2000.

Marquart, "Immobilization Techniques", SPR pages [online] Jan. 2004 pp. 1-7.

Zhang, et al., "Use of surface Plasmon resonance for the measurement of low affinity binding interactions between HSP72 and measles virus nucleocapsid protein", Biol. Proced. Online 2003;5(1):170-181.

Gestwicki, et al., "Using Receptor Conformational Change to Detect Low Molecular Weight Analytes by Surface Plasmon Resonance", Anal. Chem., 2001, 4., 5732-5737.

International Search Report dated Jul. 15, 2008 for PCT application serial No. PCT/US08/60951.

English machine translation only of JP 1993-228946 Sep. 7, 1993.

U.S. Appl. No. 12/171,475, filed Jul. 11, 2008.

\* cited by examiner

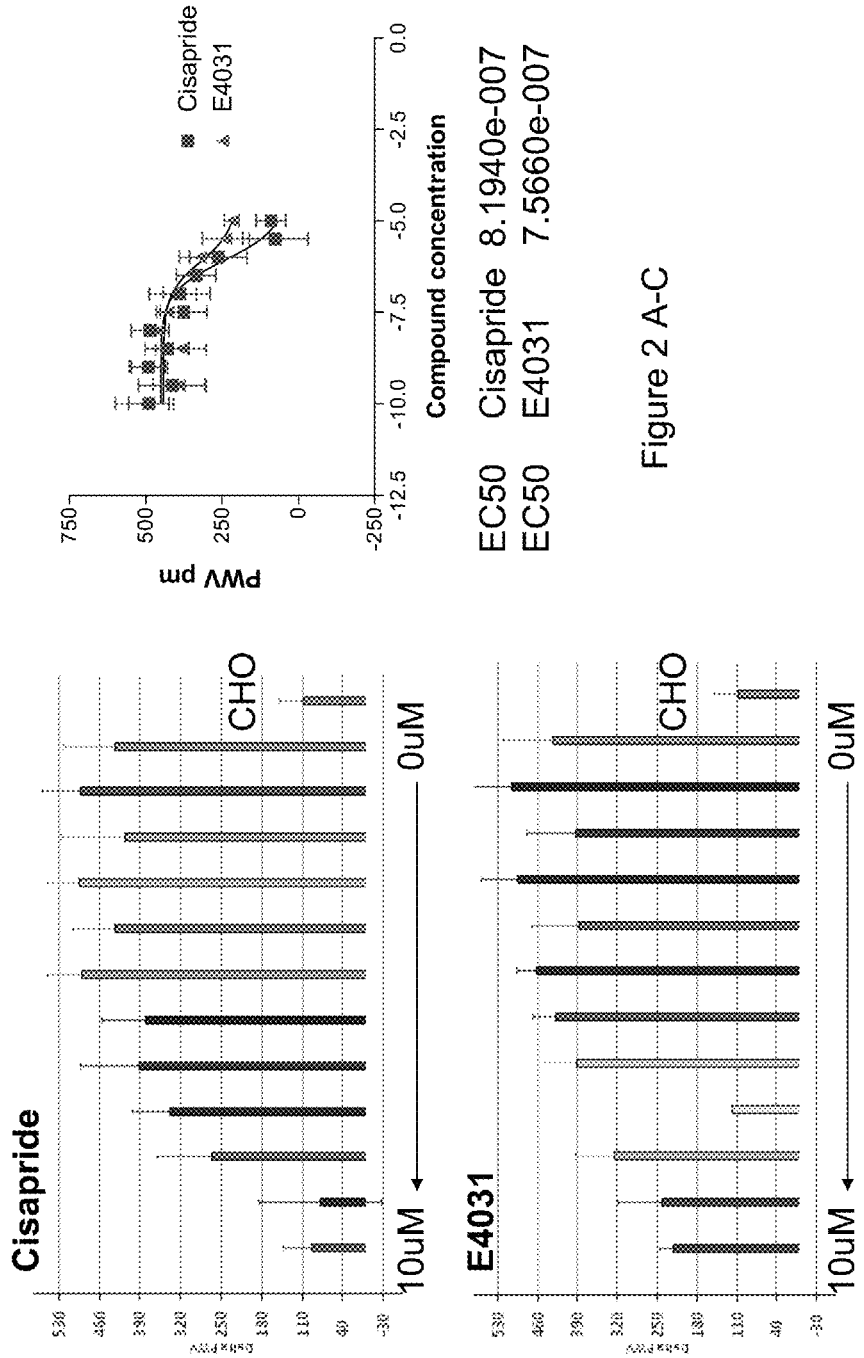
Figure 2 A-C

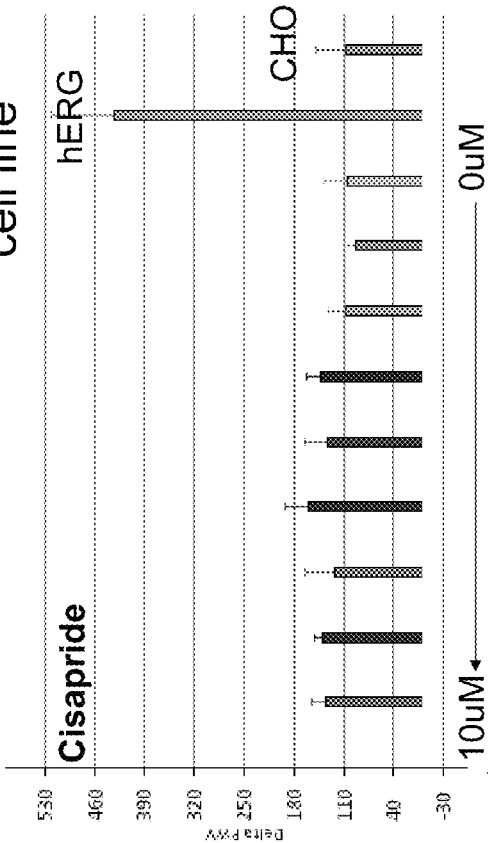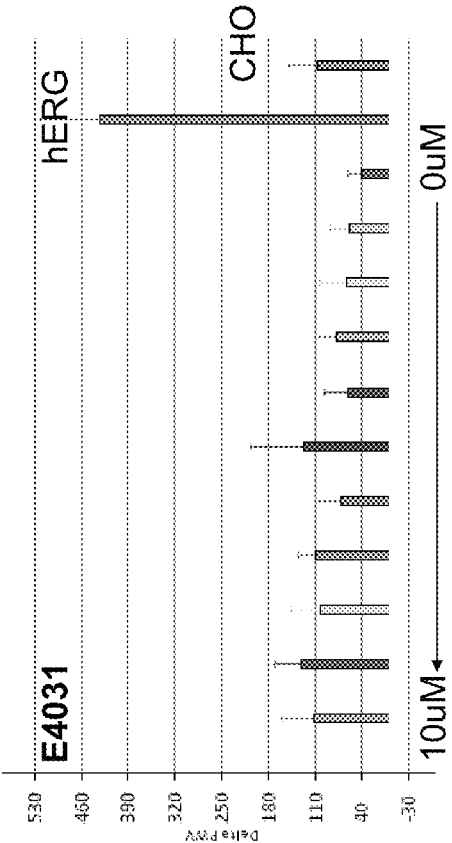

METHOD FOR DETERMINING ION CHANNEL MODULATING PROPERTIES OF A TEST REAGENT

PRIORITY

This application claims the benefit of U.S. Appl. Ser. No. 61/043,478, filed Apr. 9, 2008 and is a continuation in part of U.S. Ser. No. 12/171,475, filed on Jul. 11, 2008, which claims the benefit of U.S. Ser. No. 60/949,142, filed Jul. 11, 2007. These applications are incorporated by reference herein in their entirety. This application cross-references U.S. Ser. No. 12/335,393, entitled "Methods of Detection of Changes In Cells," filed Dec. 15, 2008, which is incorporated by reference herein in its entirety.

BACKGROUND OF THE INVENTION

Ion channels make up one of the largest classes of therapeutic targets in the pharmaceutical and biotechnology industry, especially in the areas of cardiac, pulmonary, and gastrointestinal health. The therapeutic targeting of proteins involved in regulating the flux of ions into and out of a cell have dramatic effects on patient health. Testing compounds for their ability to modulate ion channel targets can be difficult and time consuming. The patch-clamp assay is an extremely sensitive assay for the biological action of ion channel modulators. The patch-clamp method, however, is complicated and has a low throughput of test compounds.

Other methods of assaying ion channel activity require recombinant expression of the ion channel or portions of the ion channel in a cell and/or the use of fluorescent or radioactive labels. These approaches, while useful, limit access to drugs that target only a small portion of the channel functions. Furthermore, the recombinant ion channels may not function as they do in a native cell.

The methods of the current invention allow efficient high through put, label-free screening of parental (non-recombinant) cell lines without manipulation of the cells for specific response to test compounds that may be useful as drugs.

SUMMARY OF THE INVENTION

In one embodiment, the invention provides a method of identifying an antagonist or agonist of an ion channel. The method comprises applying cells to a first location and a second location on a surface of calorimetric resonant reflectance optical biosensor and applying a test reagent to the first location. A known ion channel antagonist or agonist of the cells is applied to the second location. A calorimetric resonant reflectance optical first peak wavelength value (PWV) for the first location is detected and a second PWV is detected for the second location. If the first and second PWVs are the same or similar, then the test reagent is an antagonist or agonist of an ion channel. If the first and second PWVs are different, then the test reagent is not an antagonist or agonist. The cells can be incubated for a period of time after their application to the first location; after the application of the test reagent to the first location; after the cells are applied to the second location, after the known ion channel antagonist or agonist is applied to the second location, or a combination thereof. The PWV can be detected using a scanner with a lens having a lower limit pixel size of about 2 micrometers to about 200 micrometers. The first location and second location on the surface of the calorimetric resonant reflectance optical biosensor can be an internal surface of a vessel selected from the group consisting of a microtiter well, microtiter plate, test tube, Petri dish, microfluidic channel, and microarray. The cells, test reagent, and ion channel antagonist or agonist may not comprise detection labels. The method can be performed at a temperature of about 25, 30, or 37 degrees Celsius.

Another embodiment of the invention provides a method of identifying a modulator of an ion channel. The method comprises applying cells to a first location on a surface of a calorimetric resonant reflectance optical biosensor and applying a test reagent and a known ion channel antagonist or agonist of the cells to the first location. A first PWV is determined for the first location. Cells are applied to a second location on a surface of a calorimetric resonant reflectance optical biosensor and a known ion channel antagonist or agonist of the cells is applied to the second location. A second PWV is determined for the second location. If the first and second PWVs are different, then the test reagent is a modulator of an ion channel. If the first and second PWvs are the same or similar then the test reagent is not a modulator of an ion channel. The cells can be incubated for a period of time after their application to the first location; after the application of the test reagent to the first location; after the cells are applied to the second location, after the known ion channel antagonist or agonist is applied to the second location, or a combination thereof. The PWV can be detected using a scanner with a lens having a lower limit pixel size of about 2 micrometers to about 200 micrometers. The first location and second location on the surface of the calorimetric resonant reflectance optical biosensor can be an internal surface of a vessel selected from the group consisting of a microtiter well, microtiter plate, test tube, Petri dish, microfluidic channel, and microarray. The cells, test reagent, and ion channel antagonist or agonist may not comprise detection labels. The method can be performed at a temperature of about 25, 30, or 37 degrees Celsius.

Even another embodiment of the invention provides a method for identifying a modulator of an ion channel. The method comprises applying cells to a first location on a surface of a calorimetric resonant reflectance optical biosensor and detecting a PWV for the first location. A test reagent is applied to the first location. A second PWV is detected for the first location. A first value is determined, wherein the first value is the difference between the first PWV and the second PWV. The first value is compared to a control test, wherein the control test comprises applying cells to a second location on a surface of a calorimetric resonant reflectance optical biosensor and detecting a third PWV for the second location. A known ion channel antagonist or agonist of the cells is applied to the second location. A fourth PWV for the second location is determined. A second value is determined, wherein the second value is the difference between the third PWV and the fourth PWV of the second location. If the first and second values are the same or similar, then the test reagent is a modulator of an ion channel. If the first and second values are different, then the test reagent is a not a modulator of an ion channel.

Yet another embodiment of the invention provides a method of identifying a modulator of an ion channel. The method comprises applying cells to a first location on a surface of a calorimetric resonant reflectance optical biosensor and applying a test reagent to the first location. A first PWV is determined for the first location. A known ion channel antagonist or agonist of the cells is applied to the first location. A second PWV is determined for the first location. A first value is determined, wherein the first value is the difference between the first PWV and the second PWV. Cells are applied to a second location on a surface of a calorimetric resonant reflectance optical biosensor and a third PWV for the second location is determined. A known ion channel antagonist or agonist of the cells is applied to the second location. A fourth PWV for the second location is determined. A second value is determined, wherein the second value is the difference between the third PWV and the fourth PWV. If the first and second values are different, then the test reagent is a modulator of an ion channel. If the first and second values are the same or similar, then the test reagent is not a modulator of an ion channel.

Still another embodiment of the invention provides a method of confirming that a test reagent is a modulator of an ion channel. The method comprises applying cells to a first location on a surface of a calorimetric resonant reflectance optical biosensor and detecting a first PWV for the first location. A known ion channel agonist or antagonist of the cells and a test reagent is applied to the first location. A second PWV is determined for the first location. A first value is determined, wherein the first value is the difference between the first PWV and the second PWV. Cells are applied to a second location on a surface of a calorimetric resonant reflectance optical biosensor and a third PWV is detected for the second location. A known ion channel agonist or antagonist of the cells is applied to the second location and a fourth PWV for the second location is determined. A second value is determined, wherein the second value is the difference between the third PWV and the fourth PWV. If the first and second values are different, then the test reagent is confirmed as a modulator of an ion channel. If the first and second values are the same or similar, then the test reagent is a not a modulator of an ion channel.

Yet another embodiment of the invention provides a method of confirming that a test reagent is a modulator of an ion channel. The method comprises applying cells to a first location on a surface of a calorimetric resonant reflectance optical biosensor and applying a known ion channel agonist or antagonist of the cells and the test reagent to the first location. A first PWV for the first location is determined. Cells are applied to a second location on a surface of a calorimetric resonant reflectance optical biosensor and a known ion channel agonist or antagonist of the cells is applied to the second location. A second PWV for the second location is determined. If the first and second PWVs are different, then the test reagent is confirmed as a modulator of an ion channel.

Another embodiment of the invention provides a method of determining ion channel modulating properties of a test reagent. The method comprises applying cells to a surface of a calorimetric resonant reflectance optical biosensor; substantially blocking the functional activity of one or more first types of ion channels, wherein the activity of one or more second types of ion channels is not blocked; detecting a calorimetric resonant reflectance optical first peak wavelength value (PWV) for the cells; applying a test reagent to the cells; detecting a calorimetric resonant reflectance optical second PWV for the cells; and determining ion channel modulation properties of the test reagent based on a comparison of the first PWV and second PWV. The functional activity of one or more types of ion channels can be substantially blocked by an antibody. The one or more first type and second type of ion channels can be voltage-gated sodium channels, voltage-gated calcium channels, potassium channels, inward-rectifier potassium channels, calcium-activated potassium channels, voltage-gated potassium channels, two pore domain potassium channels, transient receptor potential channels, cation channels of sperm, cyclic nucleotide gated channels, hyperpolaraization activated cyclic nucleotide gated channels, two pore channels, ligand gated channels, and light-gated channels. The cells can be incubated for a period of time after each step of the method. The surface of the calorimetric resonant reflectance optical biosensor can be an internal surface of a vessel selected from the group consisting of a microtiter well, microtiter plate, test tube, Petri dish, microfluidic channel, and microarray. The first and second PWVs can be detected using a scanner with a lens having a lower limit pixel size of about 2 micrometers to about 200 micrometers. The cells and test reagent may not comprise detection labels. The method can be performed at a temperature of about 2, 10, 15, 25, 30, or 37 degrees Celsius. The method can further comprising the steps of washing the cells; equilibrating the cells and optionally repeating the steps of the assay.

Still another embodiment of the invention provides a method of identifying a modulator of an ion channel. The method comprises applying cells in a serum-free medium to a surface of a calorimetric resonant reflectance optical biosensor, wherein one or more extracellular matrix (ECM) ligands are immobilized to the surface of the biosensor; detecting a calorimetric resonant reflectance optical first peak wavelength value (PWV) for the cells; applying one or more test ion channel modulators to the surface of the biosensor; effecting a change in the activity of one or more ion channels of the cells; detecting a calorimetric resonant reflectance optical second PWV for the cells; and determining if the one or more test ion channel modulators modulated the one or more ion channels of the cells. The method can further comprise the steps of: washing the cells; equilibrating the cells; and optionally repeating the steps of the assay.

Yet another embodiment of the invention provides a method of identifying a modulator of an ion channel. The method comprises applying cells in a serum-free medium to a surface of a calorimetric resonant reflectance optical biosensor, wherein one or more extracellular matrix (ECM) ligands are immobilized to the surface of the biosensor; applying one or more test ion channel modulators to the surface of the biosensor; effecting a change in one or more ion channels of the cells; detecting a calorimetric resonant reflectance optical first PWV for the cells; effecting a change in one or more ion channels of the cells; detecting a calorimetric resonant reflectance optical second PWV for the cells; and determining if the one or more test ion channel modulators modulated the one or more ion channels of the cells. The method can further comprising the steps of: washing the cells; equilibrating the cells; and optionally repeating the steps.

Therefore, the invention provides methods for identifying and confirming modulators of ion channels without the use of recombinant cell lines over-expressing the ion channel proteins or the use of detection labels.

BRIEF DESCRIPTION OF THE DRAWINGS

FIG. 2 demonstrates the effect of cisapride and E4031 on CHO cells transfected with hERG.

FIG. 3 demonstrates the effect of cisapride and E4031 on parental CHO cells.

DETAILED DESCRIPTION OF THE INVENTION

Figure 1:
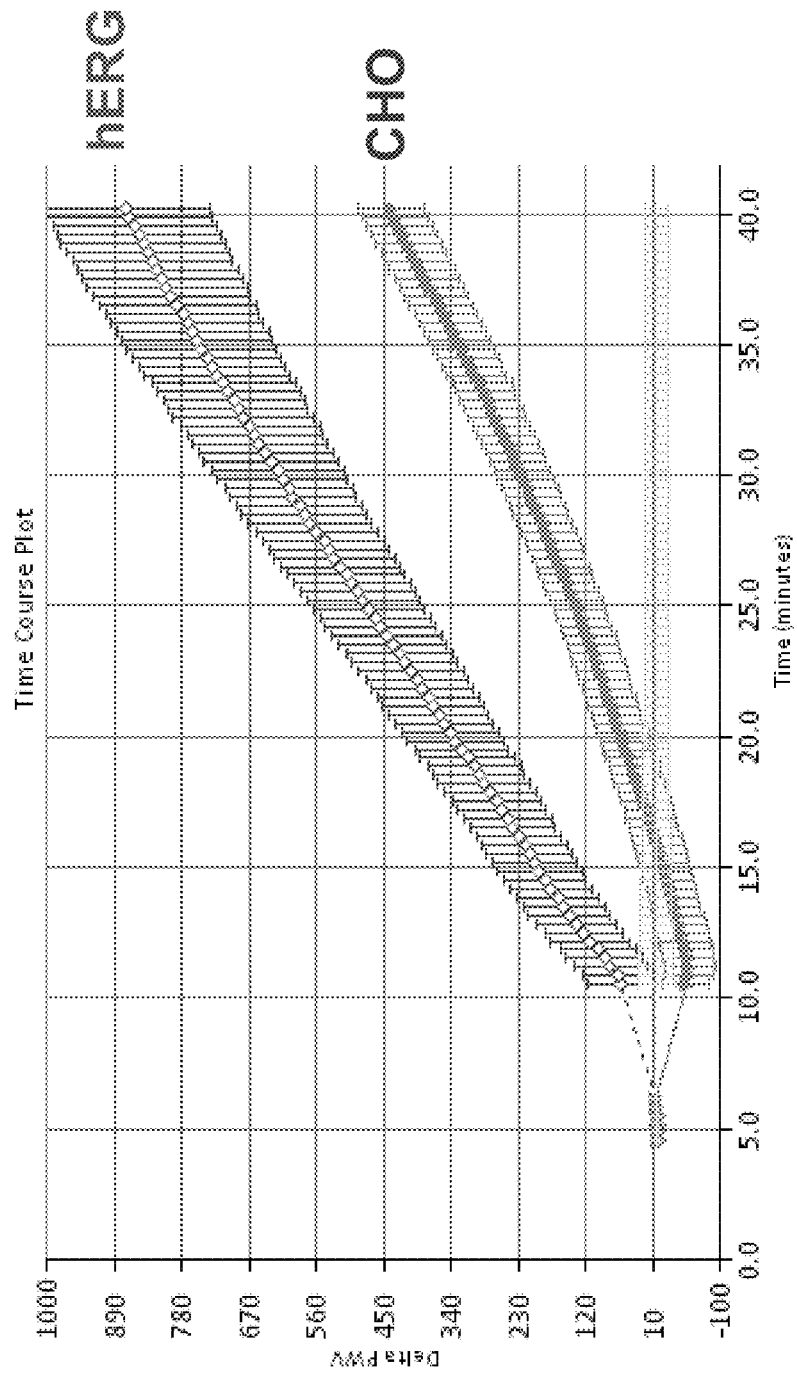
FIG. 1 demonstrates the effect of removing potassium from CHO cells transfected with the human ether-a-go-go (hERG) potassium channel and from parental CHO cells.

As used herein, the singular forms "a," "an", and "the" include plural referents unless the context clearly dictates otherwise.

Several types of ion channels are known including, e.g., voltage-gated sodium channels (that sense the transmembrane potential and open or close in response to depolarization or hyperpolarization), voltage-gated calcium channels, mechano-sensitive ion channels, potassium channels (such as, inward-rectifier potassium channels, calcium-activated potassium channels, voltage-gated potassium channels, and two pore domain potassium channels), transient receptor potential channels, cation channels of sperm, cyclic nucleotide gated channels (such as hyperpolaraization activated cyclic nucleotide gated channels)(that open in response to internal solutes and mediate cellular responses to second messengers), stretch activated channels (that open or close in response to mechanical force) two pore channels, ligand gated channels (which open in response to a specific ligand molecule on the external face of the membrane), G-protein gated channels (that open in response to G-protein-activation via its receptor), inward rectifier K channels (that allow potassium to flow into the cell in an inwardly rectifying manner), and light-gated channels. Some channels respond to multiple influences.

Ligand gated ion channels open in response to specific ligand molecules binding to the extracellular domain of the receptor protein. Ligand binding causes a conformational change in the structure of the channel protein that leads to the opening of the channel gate and subsequent ion flux across the plasma membrane. Examples of such channels include the G-protein coupled ion channels, anion-permeable γ-aminobutyric acid-gated $GABA_{A\ or\ C}$ receptors, ionotropic glutamate-gated receptors, serotonin/5-$HT_3$ receptor, ATP-gated P2X receptors, and cation-permeable "nicotinic" acetylcholine receptor.

G-protein coupled ion channels (GPC) are stimulated when a neurotransmitter binds to the G-protein coupled receptor (GCR). This activates G-proteins, which move to another ion channel. The G-Proteins allow the channel to open and ions are able to flow across the cell membrane. Because of the movement from the receptor to the ion, the speed of the channel opening is delayed, however the channel stays open for a longer time. GPC channels, such as the GABA (subtypes A & C) and NMDA (antagonists), are likely therapeutic sites for the function of anesthetics for blocking of sensation, temporarily taken away muscle activation, and behavior modification.

Binding of GABA molecules (neurotransmitter, gamma-aminobutyric acid) to their binding sites in the extracellular part of $GABA_A$ and $GABA_C$ receptors triggers opening of a chloride ion-selective pore. The increased chloride conductance drives the membrane potential towards the reversal potential of the Cl⁻ ion in neurons, inhibiting the firing of new action potentials or nerve impulses.

Glutamate regulates ion channels and is the most abundant excitatory neurotransmitter in the mammalian nervous system. Nerve impulses trigger release of glutamate from the pre-synaptic cell. In the opposing post-synaptic cell, glutamate receptors, such as the NMDA (ligand gated ion channel) receptor, bind glutamate and are activated.

Glutamate transporters are found in neuronal and glial membranes. They rapidly remove glutamate from the extracellular space. In brain injury or disease, they can work in reverse and excess glutamate can accumulate outside cells. This process causes calcium ions to enter cells via NMDA receptor channels, leading to neuronal damage and eventual cell death.

Binding of the neurotransmitter 5-hydroxytryptamine (serotonin) to the 5-$HT_3$ receptor opens the ligand gated ion channel which in turn leads to an excitatory response in neurons. When the receptor is activated to open the ion channel by agonists. 5-$HT_3$ antagonists include ondansetron, granisetron, and tropisetron.

P2X receptors are cation-permeable ligand gated ion channels that open in response to the binding of extracellular adenosine 5'-triphosphate (ATP). ATP binds to the P2X receptor and cause a conformational change in the structure of the ion channel that results in the opening of the ion-permeable pore. This allows cations such as $Na^+$ and $Ca^{2+}$ to enter the cell, leading to depolarization of the cell membrane and the activation of various $Ca^{2+}$-sensitive intracellular processes. The different protein parts of this channel have been found responsible for regulating ATP binding, ion permeation, pore dilation and desensitization.

Acetylcholine can open ligand gated sodium channels when it binds to acetylcholine receptors on skeletal muscle fibers.

Inward rectifying potassium ($K_{ir}$) channels are found on multiple cell types. In cardiac myocytes $K_{ir}$ channels close upon depolarization, slowing membrane repolarization and helping maintain a more prolonged action potential. This type of inward-rectifier channel is distinct from delayed rectifier $K^+$ channels, which help re-polarize nerve and muscle cells after action potentials; and potassium leak channels, which provide much of the basis for the resting membrane potential. In endothelial cells $K_{ir}$ channels are involved in regulation of nitric oxide synthase. In kidney cells $K_{ir}$ export surplus potassium into collecting tubules for removal in the urine, or alternatively may be involved in the reuptake of potassium back into the body. In neurons and heart cells G-protein activated IRKs ($K_{ir}3$) are important regulators. In pancreatic beta cells $K_{ATP}$ channels control insulin release.

Calcium voltage gated ion channels (VDCC) play an important role in both linking muscle excitation with contraction as well as neuronal excitation with transmitter release. Activation of VDCCs allows $Ca^{2+}$ entry into the cell, which depending on the cell type, results in muscular contraction, excitation of neurons, up-regulation of gene expression, or release of hormones or neurotransmitters.

Voltage-gated sodium channels control and set action potentials across cell membranes. When voltage-gated sodium channels open there is a change in the cell's membrane potential, and a small but significant number of $Na^+$ ions will move into the cell down their electrochemical gradient, thereby depolarizing the cell. Intracellular and extracellular blockers are known modulators of pharmacologic control of these ion channels. Alkaloid based toxins of plants and animals (puffer fish and blue-ringed octopus) act extracellularly on these channels and result in loss of neural activity. Intracellular blockage of these channels result in anesthetics, anti-arrhythmic and anti-convulsant agents. Agonists of these channels (such as the poison arrow frog toxin) directly affect the peripheral nervous system and lead to persistent activation (open) channels, and present as toxins leading to cardiac arrhythmia and respiratory paralysis.

Some transient receptor potential channels (TRP) channels can be constitutively open, while others are gated by voltage, intracellular $Ca^{2+}$, pH, redox state, osmolarity, and mechanical stretch. These channels vary according to the ion(s) they pass, some being selective for $Ca^{2+}$ while others are less selective, acting as cation channels. This family is subdivided into 6 subfamilies based on homology TRPC (canonical); TRPV (vanilloid); TRPA (ankyrin); TRPM (melastatin); TRPP (polycystin); TRPML (mucolipin); TRPN (NOMPC).

Certain chemicals and genetic disorders interfere with normal ion channel function and cause disease and illness. Chemicals that can disrupt ion channel function, include, e.g., lidocaine, novocaine, dedrotoxin, conotoxin, saxitoxin, iberiotoxin, heteropodatoxin, tetrodotoxin. Receptor tyrosine kinases, GPCRs, transient receptor potential channels, phopholipase C, signal transduction pathways (e.g. P13 kinases), cytokines, beta-arrestin pathway responses, cytoskeletal rearrangements, epigenetic signals can affect ion channel function.

Genetic diseases that are caused by mutations in ion channel subunits or the proteins that regulate them include, e.g., alternating hemiplegia of childhood, Bartter syndrome, Brugada syndrome, congenital hyperinsulinism, cystic fibrosis, episodic ataxia, erythromelalgia, generalized epilepsy with febrile seizures, hyperkalemic periodic paralysis, hypokalemic periodic paralysis, long QT syndrome, malignant hyperthermia, migraine, myasthenia gravis, myotonia congenita, neuromyotonia, familial hemiplegic migraine, spinocerebellar ataxia type 13, nonsyndromic deafness, paramyotonia congenita, potassium aggravated myotonias, periodic paralysis, retinitis pigmentosa, mucolipidosis type IV, Romano-Ward syndrome, short QT syndrome, and Timothy syndrome. Therefore, discovery of reagents that can modulate ion channels are of great interest to researchers.

One embodiment of the invention allows the direct detection of cell changes in response to ion channel regulators as they occur in real time with a colorimetric resonant reflectance biosensor and without the need to incorporate radiometric, colorimetric, or fluorescent labels. Changes in cells can be detected as the cells are probed with test reagents, agonists, and antagonists. The cellular changes can then be detected in real time using a high speed instruments such as the BIND Scanner™ (i.e., a colorimetric resonant reflectance biosensor system), and corresponding algorithms to quantify data. See, e.g., U.S. Pat. No. 6,951,715 and U.S. Pat. Publ. 2004/0151626. By combining this methodology, instrumentation and computational analyses, cellular changes can be expediently monitored in real time, in a label free manner.

Biosensors

Biosensors of the invention can be calorimetric resonant reflectance biosensors. See e.g., Cunningham et al., "Colorimetric resonant reflection as a direct biochemical assay technique," Sensors and Actuators B, Volume 81, p. 316-328, Jan. 5, 2002; U.S. Pat. Publ. No. 2004/0091397. Colorimetric resonant biosensors are not surface plasmon resonant (SPR) biosensors. SPR biosensors have a thin metal layer, such as silver, gold, copper, aluminum, sodium, and indium. The metal must have conduction band electrons capable of resonating with light at a suitable wavelength. A SPR biosensor surface exposed to light must be pure metal. Oxides, sulfides and other films interfere with SPR. Colorimetric resonant biosensors do not have a metal layer, rather they have a dielectric coating of high refractive index material, such as $TiO_2$.

Grating-based waveguide biosensors are described in, e.g., U.S. Pat. No. 5,738,825. A grating-based waveguide biosensor comprises a waveguiding film and a diffraction grating that incouples an incident light field into the waveguiding film to generate a diffracted light field. A change in the effective refractive index of the waveguiding film is detected. Devices where the wave must be transported a significant distance within the device, such as grating-based waveguide biosensors, lack the spatial resolution of the current invention.

A calorimetric resonant reflectance biosensor allows biochemical interactions to be measured on the biosensor's surface without the use of fluorescent tags, calorimetric labels or any other type of detection tag or detection label. A biosensor surface contains an optical structure that, when illuminated with collimated and/or white light, is designed to reflect only a narrow band of wavelengths ("a resonant grating effect"). The narrow wavelength band is described as a wavelength "peak." The "peak wavelength value" (PWV) changes when materials, such as biological materials, are deposited or removed from the biosensor surface. A readout instrument is used to illuminate distinct locations on a biosensor surface with collimated and/or white light, and to collect reflected light. The collected light is gathered into a wavelength spectrometer for determination of a PWV.

A biosensor can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment. Colorimetric resonant reflectance biosensors can also be incorporated into, e.g., microfluidic, macrofluidic, or microarray devices (see, e.g., U.S. Pat. No. 7,033,819, U.S. Pat. No. 7,033,821). Colorimetric resonant reflectance biosensors can be used with well-know methodology in the art (see, e.g., *Methods of Molecular Biology* edited by Jun-Lin Guan, Vol. 294, Humana Press, Totowa, N.J.) to monitor cell behavioral changes or the lack of these changes upon exposure to one or more extracellular reagents.

Colorimetric resonant reflectance biosensors comprise subwavelength structured surfaces (SWS) and are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.,* 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. Propagation of guided modes in the lateral direction are not supported. Rather, the guided mode resonant effect occurs over a highly localized region of approximately 3 microns from the point that any photon enters the biosensor structure.

The reflected or transmitted light of a calorimetric resonant reflectance biosensor can be modulated by the addition of molecules such as specific binding substances or binding partners or both to the upper surface of the biosensor. The added molecules increase the optical path length of incident radiation through the structure, and thus modify the wavelength at which maximum reflectance or transmittance will occur.

In one embodiment, a calorimetric resonant reflectance biosensor, when illuminated with white and/or collimated light, is designed to reflect a single wavelength or a narrow band of wavelengths (a "resonant grating effect"). Light can illuminate the biosensor from either the top or the bottom. When mass is deposited on the surface of the biosensor, the reflected wavelength is shifted due to the change of the optical path of light that is shown on the biosensor.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates. A single spectrometer reading can be performed in several milliseconds, thus it is possible to quickly measure a large number of molecular interactions taking place in parallel upon a biosensor surface, and to monitor reaction kinetics in real time.

A calorimetric resonant reflectance biosensor comprises, e.g., an optical grating comprised of a high refractive index material, a substrate layer that supports the grating, and optionally one or more specific binding substances or linkers immobilized on the surface of the grating opposite of the substrate layer. The high refractive index material has a higher refractive index than a substrate layer. See, e.g., U.S. Pat. No. 7,094,595; U.S. Pat. No. 7,070,987. Optionally, a cover layer covers the grating surface. In one embodiment, the refractive index of the optical grating can be less than the refractive index of the optional cover layer. An optical grating is coated with a high refractive index dielectric film which can be comprised of a material that includes, for example, zinc sulfide, titanium dioxide, tantalum oxide, silicon nitride, and silicon dioxide. A cross-sectional profile of a grating with optical features can comprise any periodically repeating function, for example, a "square-wave." An optical grating can also comprise a repeating pattern of shapes selected from the group consisting of lines (one-dimensional), squares, circles, ellipses, triangles, trapezoids, sinusoidal waves, ovals, rectangles, and hexagons. A calorimetric resonant reflectance biosensor of the invention can also comprise an optical grating comprised of, for example, plastic or epoxy, which is coated with a high refractive index material. Layer thicknesses (i.e. cover layer, biological material, or an optical grating) are selected to achieve resonant wavelength sensitivity to additional molecules on the top surface. The grating period is selected to achieve resonance at a desired wavelength.

Linear gratings (i.e., one dimensional gratings) have resonant characteristics where the illuminating light polarization is oriented perpendicular to the grating period. A calorimetric resonant reflection biosensor can also comprise, for example, a two-dimensional grating, e.g., a hexagonal array of holes or squares. Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

A colorimetric resonant reflectance biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a colorimetric resonant reflectance biosensor of the invention will be illuminated with white and/or collimated light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as an array spot or a microtiter plate well. Each separate microarray spot or microtiter plate well has a separate concentric ring pattern centered within it. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

In another embodiment, an array of holes or posts are arranged to closely approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

A detection system can comprise a calorimetric resonant reflectance biosensor a light source that directs light to the calorimetric resonant reflectance biosensor, and a detector that detects light reflected from the biosensor. In one embodiment, it is possible to simplify the readout instrumentation by the application of a filter so that only positive results over a determined threshold trigger a detection.

By measuring the shift in resonant wavelength at each distinct location of a calorimetric resonant reflectance biosensor of the invention, it is possible to determine which distinct locations have, e.g., biological material deposited on them. The extent of the shift can be used to determine, e.g., the amount of binding partners in a test sample and the chemical affinity between one or more specific binding substances and the binding partners of the test sample.

A calorimetric resonant reflectance biosensor can be illuminated two or more times. A first measurement can determine the reflectance spectra of one or more distinct locations of a biosensor with, e.g., no biological material on the biosensor or with cells on the surface. A second, third, fourth or additional measurements can determine the reflectance spectra after, e.g., one or more cells, test reagents, ion channel agonists, or ion channel antagonists are applied to a biosensor or after an incubation period or wash step. The difference in peak wavelength between these two or more measurements can be used to, e.g., determine the presence or amount of cells on the biosensor, or the activity of a test reagent, ion channel agonist, or ion channel antagonist on the cells. Additionally, this method of illumination can control for small imperfections in a surface of a biosensor that can result in regions with slight variations in the peak resonant wavelength. This method can also control for varying concentrations or density of cell matter on a biosensor.

Surface of Biosensor

One or more cells can be immobilized on a biosensor by for example, physical adsorption or by chemical binding. The cells can be non-adherent cells or adherent cells. The cells can natively express one or more ion channels or one or more ion channel components. Alternately, the cells can recombinantly express one or more ion channels or ion channel components. The cells can be mammalian cells, such as human cells.

A cell can specifically bind to a biosensor surface via a specific binding substance such as a nucleic acid, peptide, protein solution, peptide solution, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, virus, polymer or biological sample, wherein the specific binding substance is immobilized to the surface of the biosensor and the binding partner is on the surface of the cell. Alternatively, cells can grow and optionally attach on the surface of the biosensor and not necessarily be immobilized directly to the surface of the biosensor, regardless if the cell type is normally adherent or non-adherent.

Cells can be arranged in an array of one or more distinct locations on the biosensor surface, said surface residing within one or more wells of a multiwell plate and comprising one or more surfaces of the multiwell plate or microarray. The array of cells comprises one or more cells on the biosensor surface within a microwell plate such that a surface contains one or more distinct locations, each with a different cell or with a different amount of cells. For example, an array can comprise 1, 10, 100, 1,000, 10,000 or 100,000 or greater distinct locations. Thus, each well of a multiwell plate or microarray can have within it an array of one or more distinct locations separate from the other wells of the multiwell plate, which allows multiple different samples to be processed on one multiwell plate. The array or arrays within any one well can be the same or different than the array or arrays found in any other microtiter wells of the same microtiter plate.

Immobilization of a cell to a biosensor surface can be also be affected via binding to, for example, the following functional linkers: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Furthermore, a cell can be immobilized on the surface of a biosensor via physical adsorption, chemical binding, electrochemical binding, electrostatic binding, passive or active adhesion molecules, hydrophobic binding or hydrophilic binding, and immunocapture methods. Methods for coating surfaces to make them amenable to cell attachment and/or growth are well known by persons skilled in the art of cell culture and can be comprised of a coating for the biosensor with materials or their derivatives including but not limited to poly-D-lysine, fibronectin, actin, integrins, adherins, cadherins, collagen, human serum, fetal bovine serum, calf serum, laminin, or other materials.

In one embodiment of the invention a biosensor can be coated with a linker such as, e.g., a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. For example, an amine surface can be used to attach several types of linker molecules while an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal Chem.* 68, 490, (1996)).

Linkers and specific binding substances can be immobilized on the surface of a biosensor such that each well has the same linkers and/or specific binding substances immobilized therein. Alternatively, each well can contain a different combination of linkers and/or specific binding substances.

A cell can specifically or non-specifically bind to a linker or specific binding substance immobilized on the surface of a biosensor. Alternatively, the surface of the biosensor can have no linker or specific binding substance and a cell can bind to the biosensor surface non-specifically.

Immobilization of one or more specific binding substances or linker onto a biosensor is performed so that a specific binding substance or linker will not be washed away by rinsing procedures, and so that its binding to cells in a test sample is unimpeded by the biosensor surface. Several different types of surface chemistry strategies have been implemented for covalent attachment of specific binding substances to, for example, glass or polymers for use in various types of microarrays and biosensors. Surface preparation of a biosensor so that it contains the correct functional groups for binding one or more specific binding substances is an integral part of the biosensor manufacturing process.

One or more specific cells can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of specific binding substances on a biosensor surface and provide defined orientation and conformation of the surface-bound molecules.

Immobilization of specific binding substances to plastic, epoxy, or high refractive index material can be performed essentially as described for immobilization to glass. However, the acid wash step can be eliminated where such a treatment would damage the material to which the specific binding substances are immobilized.

Methods of Using Biosensors

One embodiment of the invention provides a method of identifying a modulator of an ion channel. A modulator of an ion channel has an effect on the functional activity of an ion channel. An effect on the functional activity includes blocking or inhibiting the activity of the ion channel. Modulators can block, inhibit, enhance, or increase the functional activity of an ion channel. The blocking, inhibition, enhancement or increase may take place in the presence of, or in response to, a molecule that blocks the ion channel. Modulators can, for example, act on ion channels to change gating/ligand ion selectivity, modify the chemical signals for channel function (pH, osmolarity), change the potential function for gating activity (altered polarizability or voltage dependence), cause a physical blockage, cause a physical widening (altering folding function of channel control protein), modify refractory period, modify the mechanical force function (mechanical stretch) or temperature required for channel function.

The methods of the invention can be used with cells that have not been recombinantly altered to express or over-express certain ion channels or recombinant cells, however, cells that recombinantly express or over-express ion channel proteins or subunits are not required by the methods of the invention. Cells can be applied to a first location on a surface of a calorimetric resonant reflectance optical biosensor. The cells can be immobilized to the biosensor or they can merely be grown on the surface of the biosensor. Optionally, the cells can be incubated on the surface of the biosensor at any step of the methods of the invention for about, 1, 5, 10, 30 or more minutes or about 1, 2, 5, 24, 48, 36, or more hours. The assays can be performed at a temperature of about 2, 5, 10, 25, 30, or 37 degrees Celsius (or any range of temperatures between about 2 and about 37 degrees Celsius).

Advantageously, once an assay of the invention is completed, the cells can be washed, equilibrated and used again to complete the same assay or a different assay. This is particularly advantageous where cells are expensive or difficult to handle.

In one embodiment of the invention, a method of identifying an antagonist or agonist of an ion channel is provided. The method comprises applying cells to a first location and a second location on a surface of calorimetric resonant reflectance optical biosensor. The cells can be applied to the second location at the same time the first set of cells are applied to the first location or at an earlier or later time. These cells can be the same type of cells or different cells as the set of cells applied to the first location. A test reagent is added to the first location before the cells are added to the first location, at the same time the cells are added to the first location, or after the cells are added to the first location. A known ion channel antagonist or agonist of the cells is added to the second location. The known ion channel agonist or antagonist is added to the second location before the cells are added to the second location, at the same time the cells are added to the second location, or after the cells are added to the second location. The use of known agonists or antagonists can determine the specificity of the ion channel. Antagonists and agonists, including, e.g., specific toxins and other small molecules with known functions or known target can be used to determine the specificity of the test reagent/stimuli/modulator response on an ion channel. Furthermore, use of compounds that act at sites upstream or downstream of an ion channel can be used to determine the specificity of the response to a particular channel as well. A calorimetric resonant reflectance optical first peak wavelength value (PWV) for the first location and detecting a calorimetric resonant reflectance optical second PWV for the second location, wherein if the first and second PWVs are the same or similar, then the test reagent is an antagonist or agonist of an ion channel. The first and second values are the same or similar if they are within about 1 nm or less of each other. If the first and second PWVs are substantially different (that is the first and second PWVs differ by greater than about 1 nm, 2 nm, 3 nm, 4 nm or more), then the test reagent is not an antagonist or agonist. Furthermore, one of more additional PWVs may be determined before or after any of the steps or additions of the method and compared to any other PWV.

In another embodiment of the invention, a method of identifying an antagonist or agonist of an ion channel is provided. The method comprises applying cells to a first location. A PWV can be determined for the first location. A test reagent is applied to the first location. The cells and test reagent can be incubated for period of time if desired. A second PWV for the first location can be determined. A first value can be calculated, wherein the first value is the difference between the first PWV and the second PWV. The first value can be compared to a control test. The control test can comprise applying cells to a second location on a surface of a calorimetric resonant reflectance optical biosensor. The cells can be incubated for a period of time if desired. These cells can be applied to the second location at the same time the first set of cells are applied to the first location or at an earlier or later time. These cells can be the same type of cells or different cells as the set of cells applied to the first location. A third PWV for the second location can be detected. A known ion channel antagonist or agonist of the cells is applied to the second location. The cells can be incubated for a period of time if desired. A fourth PWV for the second location can be detected. A second value can be determined, wherein the second value can be the difference between the third PWV and the fourth PWV of the second location. If the first and second values are the same or similar, then the test reagent is a modulator of an ion channel. The first and second values are the same or similar if they are within about 1 nm or less of each other. If the first and second PWVs are substantially different (that is the first and second PWVs differ by greater than about 1 nm, 2 nm, 3 nm, 4 nm, 5 nm or more), then the test reagent is not an antagonist or agonist. Because the label free biosensor method of interrogating the cells is not destructive to the cells, the cells may be treated more than one time to look for differences over a number of minutes, hours, or days.

There are multitudes of known ion channel antagonists or agonists in the art. A small sampling of examples include calcium channel blockers (such as nisoldipine, nifedipine, nicardipine, bepridil, isradipine, nimodipine, felodipine, amlodipine, diltiazem, and verapamil), modulators of potassium ion channels (see, e.g., US 20050267089), $Na^+$ ion channel modulating compounds (see, e.g, U.S. Pat. No. 6,576,791), see also, U.S. Pat. Nos. 7,101,877; 7,057,053, US 20070004718; US 20060199848, US 20060135536, US 20050192208, US 20050026993, US 20040029937, US 20030008906.

The first location and second location on the surface of the calorimetric resonant reflectance optical biosensor can be an internal surface of a vessel selected from the group consisting of a microtiter well, microtiter plate, test tube, Petri dish, microfluidic channel, and microarray. The cells, test reagent, and ion channel antagonist or agonist do not have to comprise detection labels in the assays of the invention.

Another embodiment of the invention provides a method of identifying a modulator of an ion channel. Cells can be applied to a first location on a surface of a calorimetric resonant reflectance optical biosensor. A test reagent and a known ion channel antagonist or agonist of the cells is applied to the first location. The cells, test reagent and known ion channel antagonist or agonist of the cells can be added to the sensor surface in any order or at the same time. A first PWV for the first location can be determined. Cells can be applied to a second location on a surface of a calorimetric resonant reflectance optical biosensor. The cells can be applied to the second location at the same time the first set of cells are applied to the first location or at an earlier or later time. These cells can be the same type of cells or different cells as the set of cells applied to the first location. A known ion channel antagonist or agonist of the cells is applied to the second location. The cells and known ion channel antagonist or agonist of the cells can be applied to the biosensor surface in any order or at the same time. A second PWV can be determined for the second location. If the first and second PWVs are different, then the test reagent is a modulator of an ion channel. The first and second values are different if they are greater than about 1 nm, 2 nm, 3 nm, 4 nm, 5 nm, or more apart. If the first and second PWVs are the same or similar then the test reagent is not a modulator of an ion channel. The first and second values are the same or similar if they are within about 1 nm or less of each other.

In another embodiment of the invention, a method of identifying a modulator of an ion channel is provided. The method comprises applying cells to a first location on a surface of a calorimetric resonant reflectance optical biosensor, applying a test reagent to the first location, and detecting a first PWV for the first location. The cells and test reagent can be applied to the first location in any order or at the same time. A known ion channel antagonist or agonist of the cells is then applied to the first location and a second PWV for the first location can be detected. A first value is determined wherein the first value is the difference between the first PWV and the second PWV.

The method can alternatively comprise applying cells to a first location on a surface of a calorimetric resonant reflectance optical biosensor, applying a known ion channel antagonist or agonist of the cells to the first location, and detecting a first PWV for the first location. The cells and known ion channel antagonist or agonist of the cells can be applied to the first location in any order or at the same time. A test reagent is then applied to the first location and a second PWV for the first location can be detected. A first value is determined wherein the first value is the difference between the first PWV and the second PWV.

Cells are applied to a second location on a surface of a calorimetric resonant reflectance optical biosensor. These cells can be applied to the second location at the same time the first set of cells are applied to the first location or at an earlier or later time. These cells can be the same type of cells or different cells as the set of cells applied to the first location. A third PWV for the second location can be detected. A known ion channel antagonist or agonist of the cells is applied to the second location. A fourth PWV for the second location can be determined. A second value is determined, wherein the second value is the difference between the third PWV and the fourth PWV. If the first and second values are different, then the test reagent is a modulator of an ion channel. The first and second values are different if they are greater than about 1 nm, 2 nm, 3 nm, 4 nm, 5 nm, or more apart. If the first and second values are the same or similar, then the test reagent is not a modulator of an ion channel. The first and second values are the same or similar if they are within about 1 nm or less of each other.

The cells can be incubated for a period of time after their application to the first location, after the application of the test reagent to the first location, after the application of the known ion channel agonist or antagonist to the first location, after the application of the cells to the second location, after the application of the known ion channel antagonist or agonist to the second location, or at any other point during the assay, or a combination thereof.

Optionally, the cells are incubated for a period of time after their application to a surface of the calorimetric resonant reflectance optical biosensor; after the application of the test reagent; after the application of the ion channel agonist or antagonist, or any other point during the assay, or a combination thereof. Because the label free biosensor method of interrogating the cells is not destructive to the cells, the cells may also be treated more than one time to look for differences over a number of minutes, hours, or days.

Another embodiment of the invention provides a method of confirming that a test reagent is a modulator of an ion channel comprising applying cells to a first location on a surface of a calorimetric resonant reflectance optical biosensor, and optionally detecting a first PWV for the first location. A known ion channel agonist or antagonist of the cells is applied to the first location; and the test reagent is applied to the first location. The known ion channel agonist or antagonist and the test reagent can be applied to the first location at the same time or one may be applied to the first location before the other. A second PWV can be detected for the first location. A first value can be determined, wherein the first value is the difference between the first PWV and the second PWV. Cells are applied to a second location on a surface of a calorimetric resonant reflectance optical biosensor. These cells can be applied to the second location at the same time the first set of cells are applied to the first location or at an earlier or later time. These cells can be the same type of cells or different cells as the set of cells applied to the first location. A third PWV can be determined for the second location. A known ion channel agonist or antagonist of the cells is applied to the second location and a fourth PWV can be determined for the second location. The known ion channel agonist or antagonist can be the same as that used at the first location or a different known ion channel agonist or antagonist. A second value can be determined, wherein the second value is the difference between the third PWV and the fourth PWV. If the first and second values are different, then the test reagent is confirmed as a modulator of an ion channel. The first and second values are different if they are greater than about 1 nm, 2 nm, 3 nm, 4 nm, 5 nm, or more apart.

The cells can be incubated for a period of time after their application to the biosensor; after the application of the test reagent, after the application of the known ion channel agonist or antagonist, or at any other point in the assay, or a combination thereof.

It is also useful to screen compounds to ensure that they do not modulate ion channels in any manner. There are many unintended, undesirable effects of drugs on ion channels. Several drugs have been removed from the market due to these effects (e.g., Rezulin, Loronex, Propulsid, Redux, Pondimin, Hismanal, Posicor, and Seldane). Therefore, the methods of the invention are useful to identify non-modulators of ion channels as well as modulators of ion channels.

Agonists, antagonists and modulators can affect more than one ion channel. Therefore, it can be advantageous to inhibit the function of one or more first types of ion channels in order to determine the function of an added test reagent on one or more second types of ion channels. The first and second types of ion channels can be the same or different. In one embodiment of the invention, one or more antibodies, proteins, small molecules, siRNAs, anti-sense RNAs, or other agents are used to inhibit some or all of the function of one or more types of ion channels. For example, an antibody can be specific for one or more pore subunit proteins of an ion channel such that when the antibody specifically binds to the pore protein the ion channel ceases to function in part or substantially. Once that ion channel is inhibited, a test regent, such as an agonist, antagonist, ion channel modulator, or any other compound, can be added to the cells to determine the effect of the test reagent on the non-blocked types of ion channels.

One embodiment of the invention provides a method for screening a test reagent for modulation of ion channel activity. The method can comprise contacting cells that express one or more ion channels with an agent that can partially or substantially block one or more types of ion channels. The cells are contacted with a test reagent. Ion channel activity of one or more types of ion channels can be determined before and/or after contact between the cell and the test reagent and/or before and/or after contact between the cells and the blocking agent. An alteration in ion channel activity as determined by a shift in PWV indicates that the test reagent is capable of modulating the activity of one or more types of ion channels.

A test reagent can be any molecule that potentially modulates the activity of an ion channel or alters the expression of ion channel proteins within cells. A molecule can be, for example, a polypeptide, polynucleotide, antibody, small organic molecule, polysaccharide, fatty acid, steroid, purine, pyrimidine, or multivalent cation, among others. Small organic molecules can have a molecular weight of more than 100 and less than about 2,500 Daltons (D). Preferred small molecules are less than 2000, or less than 1500 or less than 1000 or less than 500 D.

In one embodiment of the invention, one or more ECM ligands are coated on one or more surfaces of biosensor. One of more types of cells in serum-free medium are added to the surface of the biosensor. A serum-free medium contains about 5, 4, 3, 2, 1, 0.5% or less serum. A serum-free medium can comprise about 0% serum or about 0% to about 1% serum. A PWV can be determined after the addition of the cells to the biosensor. One or more potential or known modulators of ion channels can be added to the biosensor surface. A PWV can be determined after the addition of the one or more modulators. A change can be effected in the activity of one or more ion channels of the cells. For example, the cells can be depolarized.

A change in the activity of one or more ion channels can be effected by depolarizing the cells. Depolarization is a decrease in the absolute value of a cell's membrane potential. Thus, changes where the membrane potential becomes less positive or less negative are both depolarizations. Depolarization can be caused by influx of cations, e.g. $Na^+$ through $Na^+$ channels, or $Ca^{2+}$ through $Ca^{2+}$ channels. Depolarization can be inhibited by outflux of $K^+$ through $K^+$ channels. Therefore, depolarization can be caused by manipulation of salt concentration, pressure and current. See, e.g., Boulton et al. (eds), The Neuronal Microenvironment, Springer, N.Y. (1988); Arbib, The Handbook of brain theory and neural networks $2^{nd}$ Ed., MIT Press, Cambridge Mass. (2003).

Cell medium can be removed, diluted or replaced with medium with a reduced concentration of an ion, such as potassium in order to "open" ion channels. Alternatively, the cells can be exposed to an ion channel opener, e.g. scorpion venom toxin.

A PWV can be determined after the change in activity is effected in one or more ion channels (e.g., the addition of an ion channel opener). Optionally, at a pre-determined time, another change can be effected in the activity of one or more ion channels of the cells. For example, the ion concentration can be increased or voltage can be applied to effect a depolarization of the ion channel. A PWV is then determined. One of more of the PWVs can be compared to control cells, such as cells that did not have change in activity effected in one or more ion channels of the cells (e.g., no addition of an ion channel opener), cells lacking the ion channel altogether, cells receiving a channel opener, but no modulator. These responses can be measured on separate locations of the biosensor, e.g., in different wells of a microplate.

The PWVs can be compared to determine if the test ion channel modulators modulated the one or more ion channels of the cells. For example, where a test modulator of an ion channel is added to cells on a biosensor surface, a first PWV is taken, an ion channel opener is added to the cells, and a second PWV is taken, the first and second PWVs can be compared. Where the PWvs are substantially different, the test modulator has indeed modulated the ion channel. In general, resolution of differences of PWV as small as 5 pm can be detected; however, differences of greater than about 20 pm, 100 pm, 200 pm or more can also be detected. Alternatively, the PWvs can be compared to controls to determine if the test modulator has modulated the ion channels.

Where recombinant cell lines that overexpress one type of ion channel the effect of a modulator on that one type of ion channel can be determined.

In the assays of the invention before and/or after each step there can be an incubation for a period of time, a wash step, a PWV determination or a combination thereof. Optionally, a PWV reading can be taken constantly over the entire course or part of the assay.

With embodiments of the instant invention modulation of ion channels or lack thereof can be detected as it occurs, thus circumventing the need to incorporate radiometric, calorimetric, fluorescent labels or microscopy for evaluation. Changes in cells that occur due to modulation of ion channels can be expediently monitored in real time, in a label free manner. For cell changes to be detected in real time, the BIND Biosensor™, BIND Reader™, and BIND Scanner™ (e.g., a calorimetric resonant reflectance biosensor system) were designed and corresponding algorithms were created to quantify data. See, e.g., U.S. Pat. No. 6,951,715, U.S. Patent Appl. Publ. 2004/0151626.

Methods of the invention are advantageous because they do not require labeling of cells or reagents for microscopic or colorimetric/fluorimetric evaluation, they allow for continuous, multiple independent readings of the same population of cells in real time, they are quick, they require minimal reagent usage (both volume and type), they do not require recombinant cells lines, they do not require mechanical manipulation of cells, and they do not require flowing the cells through a counting device.

The label-free biosensor method is non-destructive to the cells so that a cell or a set of cells may be monitored continuously or discontinuously over a long period of time with or without treatment of known or test compounds. Methods of the invention allow for continuous monitoring or multiple independent readings of the same population of cells in real time over many days. Cellular changes can be quantified expediently and objectively over longer periods of time in a normal culturing environment (static with proper media). Methods of the invention can also be used synergistically with fluorescent labels to obtain additional, intracellular data from each cell or cell population.

Cell changes can be monitored by taking a PWV for one location over several time periods. Alternatively, scans of a receptacle holding the cells, e.g., a microtiter plate well, can be done over several time periods. In one embodiment of the invention a test reagent can be identified as a potential ion channel modulator by comparing its PWV pattern over time to a known ion channel modulator. When certain ion channel regulators are added to certain cell populations, the PWvs over time exhibit a particular pattern. For example, after an ion channel modulator is added to cells the PWV may increase for a particular period of time and then decrease. Test reagents that exhibit the same pattern of PWV values over time can be identified as a potential ion channel regulator or modulator.

One or more cells can be applied to a location, such as a microtiter well on a surface of a calorimetric resonant reflectance optical biosensor. A receptacle refers to one container and not a collection of containers, e.g., a multiwell plate. A calorimetric resonant reflectance optical peak wavelength value (PWV) for the location is detected. The one or more cells can be incubated for a period of time (e.g., 1 second, 30 seconds, 1, 2, 5, 10, 20, 30, 45 minutes, 1, 2, 5, 10 or more hours). Prior to the incubation, or after the incubation, or prior to the incubation and after the incubation one or more test reagents, ion channel agonists, and/or ion channel antagonists, can be applied to the one or more cells. The calorimetric resonant reflectance optical PWV for the location can be detected for a second time. If a change in the cells occurs then the reflected wavelength of light is shifted as compared to a situation where no change occurs. The first PWV can be compared to the second PWV. A change in the PWV can indicate a change in the cells. PWvs over several time periods can be determined and compared.

Cell changes at a biosensor location can be detected via the PWvs of the biosensor surface or monitored more generally using a microscope, digital camera, conventional camera, or other visualization apparatus, magnifying or non-magnifying, that utilizes lens-based optics or electronics-based charge coupled device (CCD) technology.

The changes in PWV can be determined using a BIND Reader®, Scanner, or Cartridge Reader. In the case of the BIND Reader and Cartridge Reader, assays can be completed in about 0.0005 to 8 hours.

Preferably, the resolution of the lens of the scanner determining the PWV has an about 2 to about 200, about 2 to about 50, or about 2 to about 15 micrometer pixel size. Assays of the invention can be completed in less than about 0.25, 0.5, 0.75, 1, 2, 3, 4, 5, 6, 7, or 8 hours. That is, cell changes in response to, for example, the added reagent can be determined in a time efficient manner.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims. In addition, where features or aspects of the invention are described in terms of Markush groups or other grouping of alternatives, those skilled in the art will recognize that the invention is also thereby described in terms of any individual member or subgroup of members of the Markush group or other group.

EXAMPLE

Screening of Inhibitors of hERG Potassium Ion Channels

This protocol employs potassium free starvation buffer to depolarize cells and thereby open ion channels such that screening ion channel modulators is possible. Colorimetric resonant reflectance biosensor plates were washed with 1×PBS for hydration baseline for 3 to 5 minutes. A PWV was determined for each of the wells. This PWV can be useful to make sure that the biosensor is stable (not drifting) and is uniform in signal across the wells. The plates were coated with 25.0 µl/well of fibronectin for 2 hrs at room temperature. The plates were blocked for 1 hour at room temperature or overnight at 4° C. by addition of 25.0 µl ovalbumin or BSA in PBS to the wells previously coated with fibronectin.

Starvation buffers were prepared with and without potassium. For 500.0 ml potassium-free starvation buffer the following reagents were used: 25 ml of 3M NaCl for 150 mM NaCl final; 10.0 ml for 20 mM HEPES; 1.0 ml for 2 mM calcium chloride; 0.5 ml for 2 mM magnesium chloride; 1.0 ml for 5 mM D-(+)-glucose; up to 500.0 ml with $H_2O$ HPLC. Potassium starvation buffer is prepared the same as above, but with 2 mM KCl added.

10 mM stocks of test compounds are diluted to 10 µM in potassium-free buffer as first concentration in an 8-point dilution series with serial $\frac{1}{3}^{rd}$ dilutions to make reagent plates: Cisapride monohydrate–10 mM=10 mg/2.06 ml DMSO for a final DMSO percentage of 0.1 to 0.5 within the cells; the titration for E4031 was started at a high concentration of 30 uM.

Cells (CHO cells transfected with the human ether-a-go-go (hERG) potassium channel or CHO parental cells) were harvested for 5-10 minutes with 3.0 mL versene/flask. The versene was deactivated with 8.0 mL full media with FBS per flask. The biosensor plates were equilibrated to room temperature and previously added PBS was removed. The cells were gently spun down for 5 minutes at 1K rpm. The media was aspirated and potassium-containing starvation buffer was added to the cell pellet. The cells were then diluted from their initial concentration to a concentration of $10^6$ cells per ml for 20,000 cells per 20.0 µl.). A baseline PWV for each well of the biosensor plate was taken as a quality control step to check for cell adhesion uniformity following a sufficient amount of time for the cells to settle and become attached.

20.0 µl of potassium-containing starvation buffer was added to each well. A PWV was taken for each well. The average number of cells/well was determined. For seeding 20K cells in 20.0 µl per well, cells were prepared at $10^6$ cells/ml. 20.0 µl of cells were added to the well already containing 20.0 µl media/buffer.

The seeded biosensor test plates were allowed to sit at room temperature for about 15 minutes, before being placing in the 37° C. incubator for 120 minutes for settling, attachment, and cell health recovery. For transfected cells, the plates were placed in the 30° C. incubator to aid protein refolding. Optionally, PWVs can be obtained for the freshly seeded biosensor plates during this time to monitor cell adherence.

In order to observe the effects of hERG channel inhibitors that prevent the hERG ion channel from opening, the cells are first be pre-incubated with inhibitor in media containing potassium. Then the cells are observed in ion channel opening conditions such as with removal of extracellular potassium or by the addition of a compound such as mallotoxin, specific for opening K+ channels. Those cells pre-incubated with inhibitor in the presence of potassium should not open under potassium-free conditions (that normally causes electrostatic potential leading to pore opening) or with lower amounts of mallotoxin. In striking comparison, those cells not exposed to inhibitor should open and a change in PWV should result indicative of normal channel function.

PWVs are taken for the biosensor plates for 3 to 5 minutes or until a stable read of less than 1-2 pm change/minute is attained. An appropriate volume of ligand or test reagent from the reagent plates was added to the biosensor plates. The cells were incubated for about 15-30 minutes. The entire volume of potassium-containing starvation buffer containing the inhibitor was replaced with the same volume of potassium-free starvation buffer containing the same final desired concentration of ligand or test reagent to the wells. PWVs were taken for each of the wells. FIG. 1 demonstrates that CHO cells transfected with hERG swell faster and more than the parental CHO cells because they have more ion channels and sodium and water are able to move into the cell quicker than in the parental CHO cells. FIGS. 2A-C demonstrate the effect of two potassium channel inhibitors (Cisapride monohydrate and E4031) on the cells. The greater the concentration of the inhibitor, the less the swelling of the cells in response to the lack of potassium. The parental CHO lines show little to no effect in the presence of the inhibitors due to the lack of the hERG ion channels. See FIG. 3.

We claim:

1. A method of determining ion channel modulating properties of a test reagent comprising:
   (a) applying cells to a surface of a colorimetric resonant reflectance optical biosensor;
   (b) substantially blocking the functional activity of one or more first types of ion channels, wherein the activity of one or more second types of ion channels is not blocked;
   (c) detecting a colorimetric resonant reflectance optical first peak wavelength value (PWV) for the cells;
   (d) applying a test reagent to the cells;
   (e) detecting a colorimetric resonant reflectance optical second PWV for the cells; and
   (f) determining any ion channel modulation properties of the test reagent based on a comparison of the first PWV and second PWV.

2. The method of claim 1, wherein the functional activity of one or more types of ion channels is substantially blocked by an antibody, protein, or small organic molecule.

3. The method of claim 1, wherein the one or more first type of ion channels are voltage-gated sodium channels, voltage-gated calcium channels, mechano-sensitive channels, potassium channels, inward-rectifier potassium channels, calcium-activated potassium channels, voltage-gated potassium channels, two pore domain potassium channels, transient receptor potential channels, cation channels of sperm, cyclic nucleotide gated channels, hyperpolaraization activated cyclic nucleotide gated channels, two pore channels, ligand gated channels, and light-gated channels.

4. The method of claim 1, wherein the one or more second type of ion channels are voltage-gated sodium channels, voltage-gated calcium channels, mechano-sensitive channels, potassium channels, inward-rectifier potassium channels, calcium-activated potassium channels, voltage-gated potassium channels, two pore domain potassium channels, transient receptor potential channels, cation channels of sperm, cyclic nucleotide gated channels, hyperpolaraization activated cyclic nucleotide gated channels, two pore channels, ligand gated channels, and light-gated channels.

5. The method of claim 1, wherein the cells are incubated for a period of time after: (a) their application to the surface; (b) the blocking the functional activity of one or more first types of ion channels; (c) after the detecting the first PWV for the cells; (d) after the application of the test reagent to the cells; (e) after the detecting the first PWV for the cells, or (f) a combination thereof.

6. The method of claim 1, wherein the surface of the colorimetric resonant reflectance optical biosensor is an internal surface of a vessel selected from the group consisting of a microtiter well, microtiter plate, test tube, Petri dish, microfluidic channel, and microarray.

7. The method of claim 1, wherein the first and second PWVs are detected using a scanner with a lens having a lower limit pixel size of about 2 micrometers to about 200 micrometers.

8. The method of claim 1, wherein the cells and test reagent do not comprise detection labels.

9. The method of claim 1, wherein the method is performed at a temperature of about 2, 10, 15, 25, 30, or 37 degrees Celsius.

10. The method of claim 1, further comprising the steps of:
    (g) washing the cells;
    (h) equilibrating the cells;
    (i) optionally repeating steps (a)-(f).

11. The method of claim 1, wherein the cells are non-recombinant cells.

12. The method of claim 1, wherein the surface of a colorimetric resonant reflectance optical biosensor is coated with fibronectin prior to the application of the cells to the biosensor.

13. The method of claim 1, wherein the surface of a colorimetric resonant reflectance optical biosensor is coated with cadherin prior to the application of the cells to the biosensor.

14. The method of claim 1, wherein the surface of a colorimetric resonant reflectance optical biosensor is coated with collagen prior to the application of the cells to the biosensor.

15. The method of claim 1, wherein the test reagent is applied to the cells in a potassium-free starvation buffer comprising 150 mM NaCl, 20 mM HEPES, 2 mM calcium chloride; 2 mM magnesium chloride; 5 mM D-(+)-glucose and no potassium.

16. The method of claim 1, wherein the test reagent is a molecule that potentially modulates the activity of an ion channel or alters the expression of ion channel proteins within cells.

17. The method of claim 1, wherein the test reagent a molecule that potentially modulates the activity of an ion channel or alters the expression of ion channel proteins within cells selected from the group consisting of a polypeptide, polynucleotide, antibody, small organic molecule, polysaccharide, fatty acid, steroid, purine, pyrimidine, and multivalent cations.

* * * * *